US006361964B1

(12) United States Patent
Kaiser et al.

(10) Patent No.: US 6,361,964 B1
(45) Date of Patent: Mar. 26, 2002

(54) EUKARYOTIC DISULFIDE BOND-FORMING PROTEINS AND RELATED MOLECULES AND METHODS

(75) Inventors: Chris A. Kaiser; Alison R. Frand, both of Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/131,750

(22) Filed: Aug. 10, 1998

Related U.S. Application Data

(60) Provisional application No. 60/055,586, filed on Aug. 12, 1997.
(51) Int. Cl.[7] .......................... C12P 21/06; C12P 19/34; C12N 9/90; A61K 14/00; C07H 21/02
(52) U.S. Cl. .................. 435/68.1; 435/6; 435/69.1; 435/91.1; 435/233; 435/252.3; 435/320.1; 536/23.1; 536/23.2; 530/300; 530/350
(58) Field of Search ................ 435/68.1, 91.1, 435/233, 252.3, 320.1, 6, 69.1; 536/23.2, 23.1; 530/350, 300

(56) References Cited

U.S. PATENT DOCUMENTS

| 5,639,635 A | 6/1997 | Joly et al. ............ 435/69.7 |
| 5,789,199 A | 8/1998 | Joly et al. ............ 435/69.1 |

OTHER PUBLICATIONS

Bowman, S. Accession No. S58198. Sequence Alignment of S58198 and Applicants' SEQ ID NO : 2, Jan. 13, 1996.*
Bardwell et al., "A pathway for disulfide bond formation in vivo." *Proc. Natl. Acad. Sci. U.S.A.* 90:1038–1042 (1993).
Bardwell et al., "Identification of a protein required for disulfide bond formation in vivo." *Cell* 67: 581–589 (1991).
Laboissiere et al., "The essential function of protein–disulfide isomerase is to unscramble non–native disulfide bonds." *J. Biol. Chem.* 270:28006–28009 (1995).
Lamantia and Lennarz, "The essential function of yeast protein disulfide isomerase does not reside in its isomarase activity." *Cell* 74:899–908 (1993).
Ng et al., "Cloning and expression of the gene for a protein disulfide oxidoreductase from *Azotobacter vinelandii*: complementation of an *Escherichia coli* dsbA mutant strain." *Gene* 188: 109–113 (1997).
Ruddock et al., "pH–dependence of the dithiol–oxidizing activity of DsbA ( a periplasmic protein thiol: disulphide oxidoreductase) and protein disulphide–isomerase: studies with a novel simple peptide subsrate." *Biochem. J.* 315:1001–1005 (1996).
Tachibana and Stevens, "The yeast EUG1 gene encodes an endoplasmic reticulum protein that is functionally related to protein disulfide isomerase." *Mol. Cell. Biol.* 12:4601–4611 (1992).
Tachikawa et al., "Isolation and characterization of a yeast gene, MPD1, the overexpression of which suppresses inviability caused by protein disulfide isomerase depletion." *FEBS Lett.* 369:212–216 (1995).

* cited by examiner

*Primary Examiner*—Tekchand Seldha
(74) *Attorney, Agent, or Firm*—Clark & Elbing LLP

(57) ABSTRACT

Disclosed herein are expression systems that make use of Ero1 to enhance disulfide bond formation and thereby to increase the yield of properly folded recombinant proteins. Also disclosed herein are recombinant Ero1 polypeptides, nucleic acids, vectors, and cells for expressing such polypeptides.

10 Claims, 12 Drawing Sheets atgagattaagaaccgccattgccacactgtgcctcacggcttttacatctgcaacttcaaacaatagctacatcgccac
cgaccaaacacaaaatgcctttaatgacactcacttttgtaaggtcgacaggaatgatcacgttagtcccagttgtaacg
taacattcaatgaattaaatgccataaatgaaaacattagagatgatctttcggcgttattaaaatctgatttcttcaaa
tactttcggctggatttatacaagcaatgttcattttgggacgccaacgatggtctgtgcttaaaccgcgcttgctctgt
tgatgtcgtagaggactgggatacactgcctgagtactggcagcctgagatcttgggtagtttcaataatgatacaatga
aggaagcggatgatagcgatgacgaatgtaagttcttagatcaactatgtcaaaccagtaaaaaacctgtagatatcgaa
gacaccatcaactactgtgatgtaaatgactttaacggtaaaaacgccgttctgattgatttaacagcaaatccggaacg
atttacaggttatggtggtaagcaagctggtcaaatttggtctactatctaccaagacaactgttttacaattggcgaaa
ctggtgaatcattggccaaagatgcatttatagacttgtatccggtttccatgcctctatcggtactcacttatcaaag
gaatatttgaacacgaaaactggtaaatgggagcccaatctggatttgtttatggcaagaatcgggaactttcctgatag
agtgacaaacatgtatttcaattatgctgttgtagctaaggctctctggaaaattcaaccatatttaccagaattttcat
tctgtgatctagtcaataaagaaatcaaaaacaaaatggataacgttatttcccagctggacacaaaaattttttaacgaa
gacttagttttgccaacgacctaagtttgactttgaaggacgaattcagatctcgcttcaagaatgtcacgaagattat
ggattgtgtgcaatgtgatagatgtagattgtggggcaaaattcaaactaccggttacgcaactgccttgaaaattttgt
ttgaaatcaacgacgctgatgaattcaccaaacaacatattgttggtaagttaaccaaatatgagttgattgcactatta
cagactttcggtagattatctgaatctattgaatctgttaacatgttcgaaaaaatgtacgggaaaaggttaaacggttc
tgaaaacaggttaagctcattcttccaaaataacttcttcaacattttgaaggaggcaggcaaatcgattcgttacacca
tagagaacatcaattccactaaagaaggaaagaaaaagactaacaattctcaatcacatgtatttgatgatttaaaaatg
cccaaagcagaaatagttccaaggccctctaacggtacagtaaataaatggaagaaagcttggaatactgaagttaacaa
cgttttagaagcattcagatttatttatagaagctatttggatttacccaggaacatctgggaattatctttgatgaagg
tatacaaattttggaataaattcatcggtgttgctgattacgttagtgaggagacacgagagcctatttcctataagcta
gatatacaataa
</pre>

Fig. 1A

MRLRTAIATLCLTAFTSATSNNSYIATDQTQNAFNDTHFCKVDR
NDHVSPSCNVTFNELNAINENIRDDLSALLKSDFFKYFRLDLYKQCSFWDANDGLCLN
RACSVDVVEDWDTLPEYWQPEILGSFNNDTMKEADDSDDECKFLDQLCQTSKKPVDIE
DTINYCDVNDFNGKNAVLIDLTANPERFTGYGGKQAGQIWSTIYQDNCFTIGETGESL
AKDAFYRLVSGFHASIGTHLSKEYLNTKTGKWPNLDLFMARIGNFPDRVTNMYFNYA
VVAKALWKIQPYLPEFSFCDLVNKEIKNKMDNVISQLDTKIFNEDLVFANDLSLTLKD
EFRSRFKNVTKIMDCVQCDRCRLWGKIQTTGYATALKILFEINDADEFTKQHIVGKLT
KYELIALLQTFGRLSESIESVNMFEKMYGKRLNGSENRLSSFFQNNFFNILKEAGKSI
RYTIENINSTKEGKKKTNNSQSHVFDDLKMPKAEIVPRPSNGTVNKWKKAWNTEVNNV
LEAFRFIYRSYLDLPRNIWELSLMKVYKFWNKFIGVADYVSEETREPISYKLDIQ

```
1 Sc(73)  LLKSDFEKVFRLDFYKQCSFW    (SEQ ID NO:12)
  Tb      ITSHPYERMFKVNEDRECRYW    (SEQ ID NO:13)
  Dm      LLVKNFERFYKVNLRQECPFW    (SEQ ID NO:14)
  Hs      LLESVYFRVYKVNLKRPGPIW    (SEQ ID NO:15)

2 Sc(176) AVLIDETANPERFTGYGGKQAGQLWSTLYQDNC  (SEQ ID NO:16)
  Tb      ATYVDLLQNPEANTGYSGPKAARVWQAVY DNC  (SEQ ID NO:17)
  Hs      AEYVDLLNPERYTGVKGPDAWKEWNVLYEENG   (SEQ ID NO:18)

3 Sc(219) AKDAEYRLVSGFHASIGTHLS    (SEQ ID NO:19)
  Tb      EKALLRQLLSGLHTSITMHVA    (SEQ ID NO:20)
  Bm      EKRVFYRLISGLHSALTISIA    (SEQ ID NO:21)
  Hs      EKRAEYRLISGLHASNVHLS     (SEQ ID NO:22)

4 Sc(332) LKDEFFRSRFKNVTKIMDCVQCDRCRLMGKIQTTGYATALKILF  (SEQ ID NO:23)
  Sp      FKDSERKHFRDESRLMDCVGCDKCRLWGKVQITCYCTALKLIL   (SEQ ID NO:24)
  Tb      LVRQMKRVVHNVTTLMDCVTCEKCRAWGKIETAAALATAVLKTVF (SEQ ID NO:25)
  Hs      LKEDERLHFRNLESRTMDCVGCFKGRLMGKLBQTQGLGTALKILF  (SEQ ID NO:26)
  At      LKQHLEKQFRNLESAIMDCVGCEKCRLWGKLQILGLGTAL-LLF   (SEQ ID NO:27)
                              *      *  *          *
```

Yeast Strains

| Strain | Genotype | Source |
|---|---|---|
| CKY8 | MATα ura3-52 leu2-3, 112 | Kaiser Lab Collection |
| CKY10 | MATa ura3-52 leu2-3, 112 | " |
| CKY39 | MATα sec12-4 ura3-52 his4-619 | " |
| CKY406 | MATα suc2-Δ9 ura3-52 leu2-3, 112 | " |
| CKY560 | MATα sec6-4 ura3-52 leu2-3, 112 ade2 | This Study |
| CKY558 | MATa ero1-1 ura3-52 leu2-3, 112 ade2 | " |
| CKY559 | MATα ero1-1 ura3-52 leu2-3, 112 | " |
| CKY561 | MATa ire1-Δ:: URA3 ura3-52 leu2-3, 112 | " |
| CKY562 | MATa/α ero1-Δ::LEU2/ERO1 leu2-3, 112/leu2-3, 112 ura3-52/ura3-52 | " |
| CKY563 | MATα ero1-Δ:: LEU2 ura3-52 leu2-3, 112 [pAF82] | " |
| CKY222 | MATa kar2-159 ura3-52 leu2-3, 112 | Mark Rose (MS174) |
| CKY229 | MATa kar2-203 ura3-52 leu2-3, 112 ade2-101 | Mark Rose (MS1032) |
| CKY190 | MATα KAR2-ΔHDEL suc2-Δ9 ura3-52 leu2-3, 112 his4-619 | Mark Rose |
| CKY395 | MATα pdi1-Δ:: TRP1-PDI1-ΔHDEL leu2-3, 112::LEU2-UPRE-lacZ ura3-1 his3-11, 15 trp1-1 ade2-1 can1-100 | Caroline Shamu (CS297) |
| CKY564 | MATα pdi1-Δ::HIS3 ura3-1 leu2-3, 112 his3-11, 15 trp1-1 ade2-1 can1-100 [pCT37] | Tom Stevens |
| CKY565 | MATa/α gsh1-Δ1::URA3/gsh1-Δ1::URA3 leu2-Δ1/LEU 2 ura3-52/ura3-52 ade2-101/ade2-101 lys2-801/LYS2 trp1-Δ1/TRP1trp5/TRP5 | Martin Grey (M65312) |

Fig. 9

```
   1 CGCCGCTGGGGCCGGCCCGCACGGCTTCATCTGAGGGCGCACGGCCCGCGACCGAGCGTGCGGACTGGCCTCCCAAGCGT  80

81 GGGGCGACAAGCTGCCGGAGCTGCA ATG GGC CGC GGC TGG GGA TTC TTG TTT GGA CTC CTG GGC  144
   1                            M   G   R   G   W   G   F   L   F   G   L   L   G    13

145 GCC GTG TGG CTG CTG CAG TCG GGC CAC GGC GAG GAG CAG CGC CCG GAG ACA GCG GCA CAG  204
  14  A   V   W   L   L   Q   S   G   H   G   E   E   Q   R   P   E   T   A   A   Q    33

205 CGG TGC TTC TGC CAG GTT AGT GGT TAC CTG GAT GAC TGT ACC TGT GAT GTT GAA ACC ATC  264
  34  R   C   F   C   Q   V   S   G   Y   L   D   D   C   T   C   D   V   E   T   I    53

265 GAT AGA TTT AAT AAC TAC AGG CTT TTC CCA AGA CTA CAA AAA CTT CTT GAA AGT GAC TAC  324
  54  F   R   F   N   N   Y   R   L   F   P   R   L   Q   K   L   L   E   S   D   Y    73

325 TTT AGG TAT TAC AAG GTA AAC CTG AAG AGG CCG TGT CCT ATC TGG AAT GAC ATC AGC CAG  384
  74  F   R   Y   Y   K   V   N   L   K   R   P   C   P   I   W   N   D   I   S   Q    93

385 TGT GGA AGA AGG GAC TGT GCT GTC AAA CCA TGT CAA TCT GAT GAA GTT CCT GAT GGA ATT  444
  94  C   G   R   R   D   C   A   V   K   P   C   Q   S   D   E   V   P   D   G   I   113

445 AAA TCT GCG AGC TAC AAG TAT TCT GAA GAA GCC AAT AAT CTC ATT GAA GAA TGT GAA CAA  504
 114  K   S   A   S   Y   K   Y   S   E   E   A   N   N   L   I   E   E   C   E   Q   153

505 GCT GAA CGA CTT GGA GCA GTG GAT GAA TCT CTG AGT GAG GAA ACA CAG AAG GCT GTT CTT  564
 134  A   E   R   L   G   A   V   D   E   S   L   S   E   E   T   Q   K   A   V   L   153¦

565 CAG TGG ACC AAG CAT GAT GAT TCT TCA GAT AAC TTC TGT GAA GCT GAT GAT GAC ATT CAG  624
 154  Q   W   T   K   H   D   D   S   S   D   N   F   C   E   A   D   D   D   I   Q   173

625 TCC CCT GAA GCT GAA TAT GTA GAT TTG CTT CTT AAT CCT GAG CGC TAC ACT GGT TAC AAG  684
 174  S   P   E   A   E   Y   V   D   L   L   L   N   P   E   R   Y   T   G   Y   K   193

685 GGA CCA GAT GCT TGG AAA ATA TGG AAT GTC ATC TAC GAA GAA AAC TGT TTT AAG CCA CAG  744
 194  G   P   D   A   W   K   I   W   N   V   I   Y   E   E   N   C   F   K   P   Q   213

745 ACA ATT AAA AGA CCT TTA AAT CCT TTG GCT TCT GGT CAA GGG ACA AGT GAA GAG AAC ACT  804
 214  T   I   K   R   P   L   N   P   L   A   S   G   Q   G   T   S   E   E   N   T   233

805 TTT TAC AGT TGG CTA GAA GGT CTC TGT GTA GAA AAA AGA GCA TTC TAC AGA CTT ATA TCT  864
 234  F   Y   S   W   L   E   G   L   C   V   E   K   R   A   F   Y   R   L   I   S   253

865 GGC CTA CAT GCA AGC ATT AAT GTG CAT TTG AGT GCA AGA TAT CTT TTA CAA GAG ACC TGG  924
 254  G   L   H   A   S   I   N   V   H   L   S   A   R   Y   L   L   Q   E   T   W   273

925 CTG GAA AAG AAA TGG GGT CAC AAT GTC ACA GAG TTC CAG CAG CGC TTT GAT GGG ATT CTG  984
 274  L   E   K   K   W   G   H   N   V   T   E   F   Q   Q   R   F   D   G   I   L   293

985 ACT GAA GGA GAA GGC CCA CGA AGG CTG AGG AAC TTG TAC TTC CTG TAC CTG ATA GAG TTA 1044
 294  T   E   G   E   G   P   R   R   L   R   N   L   Y   F   L   Y   L   I   E   L   313

1045 AGG GCT CTC TCC AAA GTG CTT CCA TTT TTT GAG CGT CCA GAT TTT CAG CTC TTC ACT GGG 1104
 314  R   A   L   S   K   V   L   P   F   F   E   R   P   D   F   Q   L   F   T   G   333

1105 AAT AAA ATT CAG GAT GAG GAA AAC AAA ATG TTA CTT CTG GAA ATA CTT CAT GAA ATC AAG 1164
 334  N   K   I   Q   D   E   E   N   K   M   L   L   L   E   I   L   H   E   I   K   353
```

Fig 10 (page 1 of 2)

```
1165 TCA TTT CCT TTG CAT TTT GAT GAG AAT TCA TTT TTT GCT GGG GAT AAA AAA GAA GCA CAC 1224
 354 S   F   P   L   H   F   D   E   N   S   F   F   A   G   D   K   K   E   A   H   373

1225 AAA CTA AAG GAG GAC TTT CGA CTG CAT TTT AGA AAT ATT TCA AGA ATT ATG GAT TGT GTT 1284
 374 K   L   K   E   D   F   R   L   H   F   R   N   I   S   R   I   M   D   C   V   393

1285 GGT TGT TTT AAA TGT CGT CTG TGG GGA AAG CTT CAG ACT CAG GGT TTG GGC ACT GCT CTG 1344
 394 G   C   F   K   C   R   L   W   G   K   L   Q   T   Q   G   L   G   T   A   L   413

1345 AAG ATC TTA TTT TCT GAG AAA TTG ATA GCA AAT ATG CCA GAA AGT GGA CCT AGT TAT GAA 1404
 414 K   I   L   F   S   E   K   L   I   A   N   M   P   E   S   G   P   S   Y   E   433

1405 TTC CAT CTA ACC AGA CAA GAA ATA GTA TCA TTA TTC AAC GCA TTT GGA AGA ATT TCT ACA 1464
 434 F   H   L   T   R   Q   E   I   V   S   L   F   N   A   F   G   R   I   S   T   453

1465 AGT GTG AAA GAA TTA GAA AAC TTC AGG AAC TTG TTA CAG AAT ATT CAT TAA AGAAAACAAGCT 1527
 454 C   V   K   E   L   E   N   F   R   N   L   L   Q   N   I   H   *                470

1528 GATATGTGCCTGTTTCTGGACAATGGAGGCGAAAGAGTGGAATTTCATTCAAAGGCATAATAGCAATGACAGTCTTAAGC 1607

1608 CAAACATTTTATATAAAGTTGCTTTTGTAAAGGAGAATTATATTGTTTTAAGTAAACACATTTTTAAAAATTGTGTTAAG 1687

1688 TCTATGTATAATACTACTGTGAGTAAAAGTAATACTTTAATAATGTGGTACAAATTTTAAAGTTTAATATTGAATAAAAG 1767

1768 GAGGATTATCAAATTCATATATGATAAAAGTGAATGTTCTAAGTCTCTCAAACTAGCGGTTTATGTAATAATATGTAATA 1847

1848 TAAA   1851
```

Fig 10 (page 2 of 2)

SEQUENCE LISTING

<160> NUMBER OF SEQ ID NOS: 29

<210> SEQ ID NO 1
<211> LENGTH: 1692
<212> TYPE: DNA
<213> ORGANISM: Saccharomyces cerevisiae

<400> SEQUENCE: 1

| | | | | | |
|---|---|---|---|---|---|
| atgagataaa | gaaccgccat | tgccacactg | tgcctcacgg | cttttacatc | tgcaacttca | 60 |
| aacaatagct | acatcgccac | cgaccaaaca | caaaatgcct | ttaatgacac | tcacttttgt | 120 |
| aaggtcgaca | ggaatgatca | cgttagtccc | agttgtaacg | taacattcaa | tgaattaaat | 180 |
| gccataaatg | aaaacattag | agatgatctt | tcggcgttat | taaaatctga | tttcttcaaa | 240 |
| tactttaggc | tggatttata | caagcaatgt | tcattttggg | acgccaacga | tggtctgtgc | 300 |
| ttaaaccgcg | cttgctctgt | tgatgtcgta | gaggactggg | atacactgcc | tgagtactgg | 360 |
| cagcctgaga | tcttgggtag | tttcaataat | gatacaatga | aggaagcgga | tgatagcgat | 420 |
| gacgaatgta | agttcttaga | tcaactatgt | caaaccagta | aaaaacctgt | agatatcgaa | 480 |
| gacaccatca | actactgtga | tgtaaatgac | tttaacggta | aaaacgccgt | tctgattgat | 540 |
| ttaacagcaa | atccggaacg | atttacaggt | tatggtggta | agcaagctgg | tcaaatttgg | 600 |
| tctactatct | accaagacaa | ctgttttaca | attggcgaaa | ctggtgaatc | attggccaaa | 660 |
| gatgcatttt | atagacttgt | atccggtttc | catgcctcta | tcggtactca | cttatcaaag | 720 |
| gaatatttga | acacgaaaac | tggtaaatgg | gagcccaatc | tggatttgtt | tatggcaaga | 780 |
| atcgggaact | ttcctgatag | agtgacaaac | atgtatttca | attatgctgt | tgtagctaag | 840 |
| gctctctgga | aaattcaacc | atatttacca | gaattttcat | tctgtgatct | agtcaataaa | 900 |
| gaaatcaaaa | acaaaatgga | taacgttatt | tcccagctgg | acacaaaaat | ttttaacgaa | 960 |
| gacttagttt | ttgccaacga | cctaagtttg | actttgaagg | acgaattcag | atctcgcttc | 1020 |
| aagaatgtca | cgaagattat | ggattgtgtg | caatgtgata | gatgtagatt | gtggggcaaa | 1080 |
| attcaaacta | ccggttacgc | aactgccttg | aaaattttgt | ttgaaatcaa | cgacgctgat | 1140 |
| gaattcacca | acaacatat | tgttggtaag | ttaaccaaat | atgagttgat | tgcactatta | 1200 |
| cagactttcg | gtagattatc | tgaatctatt | gaatctgtta | acatgttcga | aaaaatgtac | 1260 |
| gggaaaaggt | taaacggttc | tgaaaacagg | ttaagctcat | tcttccaaaa | taacttcttc | 1320 |

-continued

```
aacattttga aggaggcagg caaatcgatt cgttacacca tagagaacat caattccact    1380
aaagaaggaa agaaaaagac taacaattct caatcacatg tatttgatga tttaaaaatg    1440
cccaaagcag aaatagttcc aaggccctct aacggtacag taaataaatg gaagaaagct    1500
tggaatactg aagttaacaa cgttttagaa gcattcagat ttatttatag aagctatttg    1560
gatttaccca ggaacatctg ggaattatct ttgatgaagg tatacaaatt ttggaataaa    1620
ttcatcggtg ttgctgatta cgttagtgag gagacacgag agcctatttc ctataagcta    1680
gatatacaat aa                                                        1692
```

<210> SEQ ID NO 2
<211> LENGTH: 563
<212> TYPE: PRT
<213> ORGANISM: Saccharomyces cerevisiae

<400> SEQUENCE: 2

```
Met Arg Leu Arg Thr Ala Ile Ala Thr Leu Cys Leu Thr Ala Phe Thr
 1               5                  10                  15

Ser Ala Thr Ser Asn Asn Ser Tyr Ile Ala Thr Asp Gln Thr Gln Asn
            20                  25                  30

Ala Phe Asn Asp Thr His Phe Cys Lys Val Asp Arg Asn Asp His Val
        35                  40                  45

Ser Pro Ser Cys Asn Val Thr Phe Asn Glu Leu Asn Ala Ile Asn Glu
    50                  55                  60

Asn Ile Arg Asp Asp Leu Ser Ala Leu Leu Lys Ser Asp Phe Phe Lys
65                  70                  75                  80

Tyr Phe Arg Leu Asp Leu Tyr Lys Gln Cys Ser Phe Trp Asp Ala Asn
                85                  90                  95

Asp Gly Leu Cys Leu Asn Arg Ala Cys Ser Val Asp Val Val Glu Asp
            100                 105                 110

Trp Asp Thr Leu Pro Glu Tyr Trp Gln Pro Glu Ile Leu Gly Ser Phe
        115                 120                 125

Asn Asn Asp Thr Met Lys Glu Ala Asp Ser Asp Asp Glu Cys Lys
    130                 135                 140

Phe Leu Asp Gln Leu Cys Gln Thr Ser Lys Lys Pro Val Asp Ile Glu
145                 150                 155                 160

Asp Thr Ile Asn Tyr Cys Asp Val Asn Asp Phe Asn Gly Lys Asn Ala
                165                 170                 175

Val Leu Ile Asp Leu Thr Ala Asn Pro Glu Arg Phe Thr Gly Tyr Gly
            180                 185                 190

Gly Lys Gln Ala Gly Gln Ile Trp Ser Thr Ile Tyr Gln Asp Asn Cys
        195                 200                 205

Phe Thr Ile Gly Glu Thr Gly Glu Ser Leu Ala Lys Asp Ala Phe Tyr
    210                 215                 220

Arg Leu Val Ser Gly Phe His Ala Ser Ile Gly Thr His Leu Ser Lys
225                 230                 235                 240

Glu Tyr Leu Asn Thr Lys Thr Gly Lys Trp Glu Pro Asn Leu Asp Leu
                245                 250                 255

Phe Met Ala Arg Ile Gly Asn Phe Pro Ser Arg Val Thr Asn Met Tyr
            260                 265                 270

Phe Asn Tyr Ala Val Val Ala Lys Ala Leu Trp Lys Ile Gln Pro Tyr
        275                 280                 285

Leu Pro Glu Phe Ser Phe Cys Asp Leu Val Asn Lys Glu Ile Lys Asn
    290                 295                 300
```

-continued

```
Lys Met Asp Asn Val Ile Ser Gln Leu Asp Thr Lys Ile Phe Asn Glu
305                 310                 315                 320

Asp Leu Val Phe Ala Asn Asp Leu Ser Leu Thr Leu Lys Asp Glu Phe
            325                 330                 335

Arg Ser Arg Phe Lys Asn Val Thr Lys Ile Met Asp Cys Val Gln Cys
            340                 345                 350

Asp Arg Cys Arg Leu Trp Gly Lys Ile Gln Thr Thr Gly Tyr Ala Thr
        355                 360                 365

Ala Leu Lys Ile Leu Phe Glu Ile Asn Asp Ala Asp Glu Phe Thr Lys
    370                 375                 380

Gln His Ile Val Gly Lys Leu Thr Lys Tyr Glu Leu Ile Ala Leu Leu
385                 390                 395                 400

Gln Thr Phe Gly Arg Leu Ser Glu Ser Ile Glu Ser Val Asn Met Phe
                405                 410                 415

Glu Lys Met Tyr Gly Lys Arg Leu Asn Gly Ser Glu Asn Arg Leu Ser
            420                 425                 430

Ser Phe Phe Gln Asn Asn Phe Phe Asn Ile Leu Lys Glu Ala Gly Lys
        435                 440                 445

Ser Ile Arg Tyr Thr Ile Glu Asn Ile Asn Ser Thr Lys Glu Gly Lys
    450                 455                 460

Lys Lys Thr Asn Asn Ser Gln Ser His Val Phe Asp Asp Leu Lys Met
465                 470                 475                 480

Pro Lys Ala Glu Ile Val Pro Arg Pro Ser Asn Gly Thr Val Asn Lys
                485                 490                 495

Trp Lys Lys Ala Trp Asn Glu Thr Val Asn Val Leu Glu Ala Phe
            500                 505                 510

Arg Phe Ile Tyr Arg Ser Tyr Leu Asp Leu Pro Arg Asn Ile Trp Glu
        515                 520                 525

Leu Ser Leu Met Lys Val Tyr Lys Phe Trp Asn Lys Phe Ile Gly Val
    530                 535                 540

Ala Asp Tyr Val Ser Glu Glu Thr Arg Glu Pro Ile Ser Tyr Lys Leu
545                 550                 555                 560

Asp Ile Gln

<210> SEQ ID NO 3
<211> LENGTH: 21
<212> TYPE: PRT
<213> ORGANISM: Saccharomyces cerevisiae

<400> SEQUENCE: 3

Leu Leu Lys Ser Asp Phe Phe Lys Tyr Phe Arg Leu Asp Leu Tyr Lys
1               5                   10                  15

Gln Cys Ser Phe Trp
            20

<210> SEQ ID NO 4
<211> LENGTH: 33
<212> TYPE: PRT
<213> ORGANISM: Saccharomyces cerevisiae

<400> SEQUENCE: 4

Ala Val Leu Ile Asp Leu Thr Ala Asn Pro Glu Arg Phe Thr Gly Tyr
1               5                   10                  15

Gly Gly Lys Gln Ala Gly Gln Ile Trp Ser Thr Ile Tyr Gln Asp Asn
            20                  25                  30
Cys
```

```
<210> SEQ ID NO 5
<211> LENGTH: 21
<212> TYPE: PRT
<213> ORGANISM: Saccharomyces cerevisiae

<400> SEQUENCE: 5

Ala Lys Asp Ala Phe Tyr Arg Leu Val Ser Gly Phe His Ala Ser Ile
1               5                   10                  15

Gly Thr His Leu Ser
            20

<210> SEQ ID NO 6
<211> LENGTH: 43
<212> TYPE: PRT
<213> ORGANISM: Saccharomyces cerevisiae

<400> SEQUENCE: 6

Leu Lys Asp Glu Phe Arg Ser Arg Phe Lys Asn Val Thr Lys Ile Met
1               5                   10                  15

Asp Cys Val Gln Cys Asp Arg Cys Arg Leu Trp Gly Lys Ile Gln Thr
            20                  25                  30

Thr Gly Tyr Ala Thr Ala Leu Lys Ile Leu Phe
        35                  40

<210> SEQ ID NO 7
<211> LENGTH: 12
<212> TYPE: PRT
<213> ORGANISM: Saccharomyces cerevisiae
<220> FEATURE:
<221> NAME/KEY: VARIANT
<222> LOCATION: (1)...(12)
<223> OTHER INFORMATION: Xaa = Any Amino Acid

<400> SEQUENCE: 7

Asp Leu Xaa Xaa Asn Pro Glu Xaa Xaa Thr Gly Tyr
1               5                   10

<210> SEQ ID NO 8
<211> LENGTH: 9
<212> TYPE: PRT
<213> ORGANISM: Saccharomyces cerevisiae
<220> FEATURE:
<221> NAME/KEY: VARIANT
<222> LOCATION: (1)...(9)
<223> OTHER INFORMATION: Xaa = Any Hydrophobic Amino Acid

<400> SEQUENCE: 8

Leu Xaa Ser Gly Leu His Ala Ser Ile
1               5

<210> SEQ ID NO 9
<211> LENGTH: 15
<212> TYPE: PRT
<213> ORGANISM: Saccharomyces cerevisiae
<220> FEATURE:
<221> NAME/KEY: VARIANT
<222> LOCATION: (1)...(15)
<223> OTHER INFORMATION: Xaa at 1 and 12 = Any Hydrophobic Amino Acid;
      Xaa at 6 is Any Amino Acid; Xaa at 8 is any Acidic Amino Acid; Xaa
      at 9 is Any Basic Amino Acid.

<400> SEQUENCE: 9

Xaa Met Asp Cys Val Xaa Cys Xaa Xaa Cys Arg Xaa Trp Gly Lys
1               5                   10                  15
```

-continued

```
<210> SEQ ID NO 10
<211> LENGTH: 7
<212> TYPE: PRT
<213> ORGANISM: Saccharomyces cerevisiae
<220> FEATURE:
<221> NAME/KEY: VARIANT
<222> LOCATION: (1)...(7)
<223> OTHER INFORMATION: Xaa = Any Hydrophobic Amino Acid

<400> SEQUENCE: 10

Thr Ala Leu Lys Xaa Xaa Phe
1               5

<210> SEQ ID NO 11
<211> LENGTH: 11
<212> TYPE: PRT
<213> ORGANISM: Homo sapiens

<400> SEQUENCE: 11

Glu Gln Lys Leu Ile Ser Glu Glu Asp Leu Asn
1               5                   10

<210> SEQ ID NO 12
<211> LENGTH: 21
<212> TYPE: PRT
<213> ORGANISM: Saccharomyces cerevisiae

<400> SEQUENCE: 12

Leu Leu Lys Ser Asp Phe Phe Lys Tyr Phe Arg Leu Asp Leu Tyr Lys
1               5                   10                  15

Gln Cys Ser Phe Trp
            20

<210> SEQ ID NO 13
<211> LENGTH: 21
<212> TYPE: PRT
<213> ORGANISM: Trypanosoma brucei

<400> SEQUENCE: 13

Ile Thr Ser His Pro Tyr Phe Arg Tyr Phe Lys Val Asn Leu Asp Arg
1               5                   10                  15

Glu Cys Arg Tyr Trp
            20

<210> SEQ ID NO 14
<211> LENGTH: 21
<212> TYPE: PRT
<213> ORGANISM: Drosophila melanogaster

<400> SEQUENCE: 14

Leu Leu Val Lys Asn Phe Phe Arg Phe Tyr Lys Val Asn Leu Arg Gln
1               5                   10                  15

Glu Cys Pro Phe Trp
            20

<210> SEQ ID NO 15
<211> LENGTH: 21
<212> TYPE: PRT
<213> ORGANISM: Homo sapiens
```

-continued

```
<400> SEQUENCE: 15

Leu Leu Glu Ser Val Tyr Phe Arg Tyr Tyr Lys Val Asn Leu Lys Arg
1               5                   10                  15

Pro Cys Pro Ile Trp
            20

<210> SEQ ID NO 16
<211> LENGTH: 33
<212> TYPE: PRT
<213> ORGANISM: Saccharomyces cerevisiae

<400> SEQUENCE: 16

Ala Val Leu Ile Asp Leu Thr Ala Asn Pro Glu Arg Phe Thr Gly Tyr
1               5                   10                  15

Gly Gly Lys Gln Ala Gly Gln Ile Trp Ser Thr Ile Tyr Gln Asp Asn
                20                  25                  30

Cys

<210> SEQ ID NO 17
<211> LENGTH: 32
<212> TYPE: PRT
<213> ORGANISM: Trypanosoma brucei

<400> SEQUENCE: 17

Ala Thr Tyr Val Asp Leu Leu Gln Asn Pro Glu Ala Asn Thr Gly Tyr
1               5                   10                  15

Ser Gly Pro Lys Ala Ala Arg Val Trp Gln Ala Val Tyr Asp Asn Cys
                20                  25                  30

<210> SEQ ID NO 18
<211> LENGTH: 33
<212> TYPE: PRT
<213> ORGANISM: Homo sapiens

<400> SEQUENCE: 18

Ala Glu Tyr Val Asp Leu Leu Leu Asn Pro Glu Arg Tyr Thr Gly Tyr
1               5                   10                  15

Lys Gly Pro Asp Ala Trp Lys Ile Trp Asn Val Ile Tyr Glu Glu Asn
                20                  25                  30

Cys

<210> SEQ ID NO 19
<211> LENGTH: 21
<212> TYPE: PRT
<213> ORGANISM: Saccharomyces cerevisiae

<400> SEQUENCE: 19

Ala Lys Asp Ala Phe Tyr Arg Leu Val Ser Gly Phe His Ala Ser Ile
1               5                   10                  15

Gly Thr His Leu Ser
                20

<210> SEQ ID NO 20
<211> LENGTH: 21
<212> TYPE: PRT
<213> ORGANISM: Trypanosoma brucei
```

-continued

<400> SEQUENCE: 20

Glu Lys Ala Leu Leu Arg Gln Leu Leu Ser Gly Leu His Thr Ser Ile
1               5                   10                  15

Thr Met His Val Ala
            20

<210> SEQ ID NO 21
<211> LENGTH: 21
<212> TYPE: PRT
<213> ORGANISM: Brugia malayi

<400> SEQUENCE: 21

Glu Lys Arg Val Phe Tyr Arg Leu Ile Ser Gly Leu His Ser Ala Ile
1               5                   10                  15

Thr Ile Ser Ile Ala
            20

<210> SEQ ID NO 22
<211> LENGTH: 21
<212> TYPE: PRT
<213> ORGANISM: Homo sapiens

<400> SEQUENCE: 22

Glu Lys Arg Ala Phe Tyr Arg Leu Ile Ser Gly Leu His Ala Ser Ile
1               5                   10                  15

Asn Val His Leu Ser
            20

<210> SEQ ID NO 23
<211> LENGTH: 43
<212> TYPE: PRT
<213> ORGANISM: Saccharomyces cerevisiae

<400> SEQUENCE: 23

Leu Lys Asp Glu Phe Arg Ser Arg Phe Lys Asn Val Thr Lys Ile Met
1               5                   10                  15

Asp Cys Val Gln Cys Asp Arg Cys Arg Leu Trp Gly Lys Ile Gln Thr
            20                  25                  30

Thr Gly Tyr Ala Thr Ala Leu Lys Ile Leu Phe
        35                  40

<210> SEQ ID NO 24
<211> LENGTH: 43
<212> TYPE: PRT
<213> ORGANISM: Schizosaccharomyces pombe

<400> SEQUENCE: 24

Phe Lys Asp Ser Phe Arg Lys His Phe Arg Asp Ile Ser Arg Ile Met
1               5                   10                  15

Asp Cys Val Gly Cys Asp Lys Cys Arg Leu Trp Gly Lys Val Gln Ile
            20                  25                  30

Thr Gly Tyr Gly Thr Ala Leu Lys Leu Leu Leu
        35                  40

<210> SEQ ID NO 25
<211> LENGTH: 43
<212> TYPE: PRT
<213> ORGANISM: Trypanosoma brucei

<400> SEQUENCE: 25

Leu Val Arg Gln Met Lys Arg Val Val His Asn Val Thr Thr Leu Met
1               5                   10                  15

Asp Cys Val Thr Cys Glu Lys Cys Arg Ala Trp Gly Lys Leu Glu Thr
            20                  25                  30

Ala Ala Leu Ala Thr Ala Leu Lys Ile Val Phe
        35                  40

<210> SEQ ID NO 26
<211> LENGTH: 43
<212> TYPE: PRT
<213> ORGANISM: Homo sapiens

<400> SEQUENCE: 26

Leu Lys Glu Asp Phe Arg Leu His Phe Arg Asn Ile Ser Arg Ile Met
1               5                   10                  15

Asp Cys Val Gly Cys Phe Lys Cys Arg Leu Trp Gly Lys Leu Gln Thr
            20                  25                  30

Gln Gly Leu Gly Thr Ala Leu Lys Ile Leu Phe
        35                  40

<210> SEQ ID NO 27
<211> LENGTH: 42
<212> TYPE: PRT
<213> ORGANISM: Arabidopsis thaliana

<400> SEQUENCE: 27

Leu Lys Gln His Leu Glu Lys Gln Phe Arg Asn Ile Ser Ala Ile Met
1               5                   10                  15

Asp Cys Val Gly Cys Glu Lys Cys Arg Leu Trp Gly Lys Leu Gln Ile
            20                  25                  30

Leu Gly Leu Gly Thr Ala Leu Ile Leu Phe
        35                  40

<210> SEQ ID NO 28
<211> LENGTH: 1851
<212> TYPE: DNA
<213> ORGANISM: Homo sapiens, Mus musculus, Rattus norvegius

<400> SEQUENCE: 28

```
cgccgctggg gccggcccgc acggcttcat ctgagggcgc acggcccgcg accgagcgtg      60
cggactggcc tcccaagcgt ggggcgacaa gctgccggag ctgcaatggg ccgcggctgg     120
ggattcttgt ttggactcct gggcgccgtg tgctgctgc agtcgggcca cggcgaggag     180
cagcgcccgg agacagcggc acagcggtgc ttctgccagg ttagtggtta cctggatgac     240
tgtacctgtg atgttgaaac catcgataga tttaataact acaggctttt cccaagacta     300
caaaaacttc ttgaaagtga ctactttagg tattacaagg taaacctgaa gaggccgtgt     360
cctatctgga atgacatcag ccagtgtgga agaagggact gtgctgtcaa accatgtcaa     420
tctgatgaag ttcctgatgg aattaaatct gcgagctaca gtattctga agaagccaat     480
aatctcattg aagaatgtga acaagctgaa cgacttggag cagtggatga atctctgagt     540
gaggaaacac agaaggctgt tcttcagtgg accaagcatg atgattcttc agataacttc     600
tgtgaagctg atgatgacat tcagtcccct gaagctgaat atgtagattt gcttcttaat     660
cctgagcgct acactggtta caagggacca gatgcttgga aaatatggaa tgtcatctac     720
gaagaaaact gttttaagcc acagacaatt aaaagacctt taaatccttt ggcttctggt     780
```

-continued

```
caaggacaa gtgaagagaa cactttttac agttggctag aaggtctctg tgtagaaaaa      840
agagcattct acagacttat atctggccta catgcaagca ttaatgtgca tttgagtgca      900
agatatcttt tacaagagac ctggctggaa aagaaatggg gtcacaatgt cacagagttc      960
cagcagcgct tgatgggat tctgactgaa ggagaaggcc cacgaaggct gaggaacttg      1020
tacttcctgt acctgataga gttaagggct ctctccaaag tgcttccatt ttttgagcgt      1080
ccagattttc agctcttcac tgggaataaa attcaggatg aggaaaacaa aatgttactt      1140
ctggaaatac ttcatgaaat caagtcattt cctttgcatt ttgatgagaa ttcattttt      1200 gctggggata aaaagaagc acacaaacta aaggaggact ttcgactgca ttttagaaat      1260
atttcaagaa ttatggattg tgttggttgt tttaaatgtc gtctgtgggg aaagcttcag      1320
actcagggtt tgggcactgc tctgaagatc ttattttctg agaaattgat agcaaatatg      1380
ccagaaagtg gacctagtta tgaattccat ctaaccagac aagaaatagt atcattattc      1440
aacgcatttg gaagaatttc tacaagtgtg aaagaattag aaaacttcag gaacttgtta      1500
cagaatattc attaaagaaa acaagctgat atgtgcctgt ttctggacaa tggaggcgaa      1560
agagtggaat tcattcaaa ggcataatag caatgacagt cttaagccaa acattttata      1620
taaagttgct tttgtaaagg agaattatat tgtttttaagt aaacacattt ttaaaaattg      1680
tgttaagtct atgtataata ctactgtgag taaaagtaat actttaataa tgtggtacaa      1740 atttaaagt ttaatattga ataaaggag gattatcaaa ttcatatatg ataaaagtga      1800
atgttctaag tctctcaaac tagcggttta tgtaataata tgtaatataa a              1851
```

<210> SEQ ID NO 29
<211> LENGTH: 469
<212> TYPE: PRT
<213> ORGANISM: Homo sapiens, Mus musculus, Rattus norvegius

<400> SEQUENCE: 29

```
Met Gly Arg Gly Trp Gly Phe Leu Phe Gly Leu Leu Gly Ala Val Trp
 1               5                  10                  15

Leu Leu Gln Ser Gly His Gly Glu Glu Gln Arg Pro Glu Thr Ala Ala
            20                  25                  30

Gln Arg Cys Phe Cys Gln Val Ser Gly Tyr Leu Asp Asp Cys Thr Cys
        35                  40                  45

Asp Val Glu Thr Ile Asp Arg Phe Asn Asn Tyr Arg Leu Phe Pro Arg
    50                  55                  60

Leu Gln Lys Leu Leu Glu Ser Asp Tyr Phe Arg Tyr Tyr Lys Val Asn
65                  70                  75                  80

Leu Lys Arg Pro Cys Pro Ile Trp Asn Asp Ile Ser Gln Cys Gly Arg
                85                  90                  95

Arg Asp Cys Ala Val Lys Pro Cys Gln Ser Asp Glu Val Pro Asp Gly
            100                 105                 110

Ile Lys Ser Ala Ser Tyr Lys Tyr Ser Glu Glu Ala Asn Asn Leu Ile
        115                 120                 125

Glu Glu Cys Glu Gln Ala Glu Arg Leu Gly Ala Val Asp Glu Ser Leu
    130                 135                 140

Ser Glu Thr Gln Lys Ala Val Leu Gln Trp Thr Lys His Asp Asp
145                 150                 155                 160

Ser Ser Asp Asn Phe Cys Glu Ala Asp Asp Ile Gln Ser Pro Glu
                165                 170                 175

Ala Glu Tyr Val Asp Leu Leu Leu Asn Pro Glu Arg Tyr Thr Gly Tyr
            180                 185                 190
```

-continued

```
Lys Gly Pro Asp Ala Trp Lys Ile Trp Asn Val Ile Tyr Glu Glu Asn
        195                 200                 205

Cys Phe Lys Pro Gln Thr Ile Lys Arg Pro Leu Asn Pro Leu Ala Ser
        210                 215                 220

Gly Gln Gly Thr Ser Glu Glu Asn Thr Phe Tyr Ser Trp Leu Glu Gly
225                     230                 235                 240

Leu Cys Val Glu Lys Arg Ala Phe Tyr Arg Leu Ile Ser Gly Leu His
                245                 250                 255

Ala Ser Ile Asn Val His Leu Ser Ala Arg Tyr Leu Leu Gln Glu Thr
                260                 265                 270

Trp Leu Glu Lys Lys Trp Gly His Asn Val Thr Glu Phe Gln Gln Arg
            275                 280                 285

Phe Asp Gly Ile Leu Thr Glu Gly Glu Gly Pro Arg Arg Leu Arg Asn
    290                 295                 300

Leu Tyr Phe Leu Tyr Leu Ile Glu Leu Arg Ala Leu Ser Lys Val Leu
305                 310                 315                 320

Pro Phe Phe Glu Arg Pro Asp Phe Gln Leu Phe Thr Gly Asn Lys Ile
                325                 330                 335

Gln Asp Glu Glu Asn Lys Met Leu Leu Leu Glu Ile Leu His Glu Ile
                340                 345                 350

Lys Ser Phe Pro Leu His Phe Asp Glu Asn Ser Phe Phe Ala Gly Asp
            355                 360                 365

Lys Lys Glu Ala His Lys Leu Lys Glu Asp Phe Arg Leu His Phe Arg
    370                 375                 380

Asn Ile Ser Arg Ile Met Asp Cys Val Gly Cys Phe Lys Cys Arg Leu
385                 390                 395                 400

Trp Gly Lys Leu Gln Thr Gln Gly Leu Gly Thr Ala Leu Lys Ile Leu
                405                 410                 415

Phe Ser Glu Lys Leu Ile Ala Asn Met Pro Glu Ser Gly Pro Ser Tyr
                420                 425                 430

Glu Phe His Leu Thr Arg Gln Glu Ile Val Ser Leu Phe Asn Ala Phe
            435                 440                 445

Gly Arg Ile Ser Thr Ser Val Lys Glu Leu Glu Asn Phe Arg Asn Leu
    450                 455                 460

Leu Gln Asn Ile His
465
```

EUKARYOTIC DISULFIDE BOND-FORMING PROTEINS AND RELATED MOLECULES AND METHODS

CROSS REFERENCE TO RELATED APPLICATION

This application claims benefit from U.S. provisional application, Ser. No. 60/055,586, which was filed Aug. 12, 1997.

STATEMENT AS TO FEDERALLY SPONSORED RESEARCH

This invention was made in part with support from the Government through NIH Grant No. ROI GM46941. The Government has certain rights in the invention.

BACKGROUND OF THE INVENTION

This invention relates to novel eukaryotic disulfide bond-forming proteins and uses thereof, particularly for increasing yields of recombinant proteins produced in in vivo or in vitro expression systems.

Many commercially produced proteins are cell surface or extracellular proteins that contain cysteine residues capable of forming disulfide bonds in the oxidizing environment of the endoplasmic reticulum (ER). For these proteins to assume their proper active folded conformation, the cysteine residues must be linked by disulfide bonds in a correct pairwise arrangement, a process that is catalyzed by cellular enzymes. One such enzyme involved in both the formation and rearrangement of disulfide bonds in eukaryotic cells is the abundant ER protein disulfide-isomerase (PDI). Protein production strategies to maximize the yield of disulfide bond-containing proteins have made use of PDI, either by overproducing PDI in cells expressing a protein of interest or by mixing a denatured protein substrate with purified PDI in in vitro refolding systems. In either case, even the use of excess PDI has generally resulted in only a modest increase in the yield of properly folded protein, and has sometimes catalyzed instead the formation of insoluble protein aggregates.

SUMMARY OF THE INVENTION

In general, the invention features a method of increasing disulfide bond formation in a protein (for example, a secreted protein) involving: (a) denaturing the protein; and (b) allowing renaturation of the protein in the presence of an Ero1 polypeptide (formerly known as a Sec81 polypeptide). In a preferred embodiment of this method, the Ero1 polypeptide is combined with a protein disulfide-isomerase. In another embodiment, the Ero1 polypeptide is derived from a yeast.

In another aspect, the invention features a method of increasing disulfide bond formation in a protein (for example, a secreted protein), involving expressing the protein in a host cell that also expresses an isolated nucleic acid that encodes an Ero1 polypeptide. In a preferred embodiment of this method, the host cell further expresses a nucleic acid encoding a protein disulfide-isomerase. In another embodiment, the Ero1 polypeptide is derived from a yeast.

In another aspect, the invention features a substantially pure preparation of an Ero1 polypeptide, which may be derived from a yeast or from a mammal (for example, a human). In preferred embodiments, the Ero1 polypeptide includes an amino acid sequence which is at least 27%, preferably at least 50%, more preferably at least 60%, and most preferably at least 80% identical to the amino acid sequence of SEQ ID NO: 2 or SEQ ID NO: 29, or alternatively which exhibits at least 50%, preferably, at least 70%, more preferably at least 80%, and most preferably at least 90% sequence identity to SEQ ID NOS: 3, 4, 5, 6, 7, 8, 9, or 10, or any combination thereof.

The invention also features isolated nucleic acid encoding an Ero1 polypeptide. This isolated nucleic acid is preferably at least 27%, more preferably 50%, and most preferably at least 75% identical to the nucleotide sequence of SEQ ID NO: 1 or SEQ ID NO: 28, or encodes an Ero1 polypeptide which either includes an amino acid sequence that is at least 27%, preferably at least 50%, more preferably at least 60%, and most preferably at least 80% identical to the amino acid sequence of SEQ ID NO: 2 or SEQ ID NO: 29, or exhibits at least 50%, preferably at least 70%, more preferably at least 80%, and most preferably at least 90% sequence identity to SEQ ID NOS: 3, 4, 5, 6, 7, 8, 9, or 10 or any combination thereof. This nucleic acid may include the sequence of SEQ ID NO: 1 or SEQ ID NO: 28, or, in a preferred embodiment, may complement an Ero1 mutation in yeast (for example, S. cerevisiae).

The isolated nucleic acid encoding an Ero1 polypeptide may be included in a vector, such as a vector that is capable of directing the expression of the protein encoded by the nucleic acid in a vector-containing cell. The isolated nucleic acid in the vector can be operatively linked to a promoter, for example, a promoter that is capable of overexpressing the Ero1 polypeptide, or that is capable of expressing Ero1 in a conditional manner. The isolated nucleic acid encoding an Ero1 polypeptide, or a vector including this nucleic acid, may be contained in a cell, such as a bacterial, mammalian, or yeast cell.

Also included in the invention is a method of producing a recombinant Ero1 polypeptide, and an Ero1 polypeptide produced by this method. This method involves (a) providing a cell transformed with isolated nucleic acid that encodes an Ero1 polypeptide and is positioned for expression in the cell under conditions for expressing the isolated nucleic acid, and (b) expressing the recombinant Ero1 polypeptide.

A substantially pure antibody, such as a monoclonal or polyclonal antibody, that specifically recognizes and binds an Ero1 polypeptide is also included in the invention. Preferably, the Ero1 polypeptide is derived from a yeast.

The invention also features a method of detecting a gene, or a portion of a gene, that is found in a mammalian cell (for example, a human cell) and that has sequence identity to the Ero1 sequence of FIG. 1A (SEQ ID NO: 1) or to the Ero1 sequence of FIG. 10 (SEQ ID NO: 28). In this method, isolated nucleic acid encoding the Ero1 polypeptide, a portion of such nucleic acid greater than about 15 residues in length, or a degenerate oligonucleotide corresponding to one or more Ero1 conserved domains (for example, SEQ ID NOS: 3, 4, 5, 6, 7, 8, 9, or 10), is contacted with a preparation of nucleic acid from the mammalian (for example, human) cell under hybridization conditions that provide detection of nucleic acid sequences having about 50% or greater nucleic acid sequence identity. If desired, this method may also include a step of testing the gene, or portion thereof, for the ability to functionally complement a yeast Ero1 mutant (e.g., a S. cerevisiae Ero1 mutant).

Another method included in the invention is a method of isolating a gene, or a portion of a gene, that is found in a mammalian cell (for example, a human cell) and has at least 50%, preferably at least 70%, more preferably at least 80%, and most preferably at least 90% sequence identity to a sequence encoding SEQ ID NOS: 3, 4, 5, 6, 7, 8, 9, or 10. This method involves (a) amplifying by PCR the mammalian gene, or portion thereof, using oligonucleotide primers having regions of complementarity to opposite nucleic acid strands in a region of the nucleotide sequence of FIG. 1A (SEQ ID NO: 1) or of FIG. 10 (SEQ ID NO: 28), and (b) isolating the mammalian gene, or portion thereof. This method can also include a step of testing the gene, or portion thereof, for the ability to functionally complement a yeast Ero1 mutant (e.g., a S. cerevisiae Ero1 mutant).

As used herein, by an "Ero1" polypeptide is meant a polypeptide, formerly known as a Sec81 polypeptide, derived from a eukaryote that promotes disulfide bond formation and whose function may be substituted by an exogenous oxidant, such as diamide (for example, under conditions as described herein).

By "substantially pure" is meant a preparation which is at least 60% by weight (dry weight) the compound of interest, e.g., an Ero1 polypeptide. Preferably the preparation is at least 75%, more preferably at least 90%, and most preferably at least 99% by weight the compound of interest. Purity can be measured by any appropriate method, e.g., column chromatography, polyacrylamide gel electrophoresis, or HPLC analysis.

By "isolated nucleic acid" is meant nucleic acid that is not immediately contiguous with both of the coding sequences with which it is immediately contiguous (one on the 5' end and one on the 3' end) in the naturally-occurring genome of the organism from which it is derived. The term therefore includes, for example, a recombinant nucleic acid which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant nucleic acid which is part of a hybrid gene encoding additional polypeptide sequence.

By a "substantially identical" polypeptide sequence is meant an amino acid sequence which differs from a reference sequence only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the polypeptide (assayed, e.g., as described herein).

Preferably, such a sequence is at least 75%, more preferably at least 85%, and most preferably at least 95% identical at the amino acid level to the sequence used for comparison.

Sequence identity is typically measured using sequence analysis software (e.g., Sequence Analysis Software Package of the Genetics Computer Group, University of Wisconsin Biotechnology Center, 1710 University Avenue, Madison, Wis. 53705, or BLAST software available from the National Library of Medicine). Examples of useful software include the programs, Pile-up and PrettyBox. Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By a "substantially identical" nucleic acid is meant a nucleic acid sequence which encodes a polypeptide differing only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the polypeptide (assayed, e.g., as described herein). Preferably, the encoded sequence is at least 75%, more preferably at least 85%, and most preferably at least 95% identical at the amino acid level to the sequence of comparison. If nucleic acid sequences are compared, a "substantially identical" nucleic acid sequence is one which is at least 85%, more preferably at least 90%, and most preferably at least 95% identical to the sequence of comparison. The length of nucleic acid sequence comparison will generally be at least 50 nucleotides, preferably at least 60 nucleotides, more preferably at least 75 nucleotides, and most preferably at least 100 nucleotides. Again, identity is typically measured using sequence analysis software (e.g., Sequence Analysis Software Package of the Genetics Computer Group, University of Wisconsin Biotechnology Center, 1710 University Avenue, Madison, Wis. 53705).

By "positioned for expression" is meant that the nucleic acid molecule is positioned adjacent to a sequence which directs transcription and translation of the nucleic acid molecule.

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody.

By "specifically binds" is meant an antibody which recognizes and binds an Ero1 polypeptide but which does not substantially recognize and bind other molecules in a sample (e.g., a biological sample) which naturally includes the Ero1 polypeptide. An antibody which "specifically binds" such a polypeptide is sufficient to detect protein product in such a biological sample using one or more of the standard immunological techniques available to those in the art (for example, Western blotting or immunoprecipitation).

By "complementation" is meant an improvement of a genetic defect or mutation.

The present invention provides an important advance in this field of technology. For example, the identification of Ero1 provides a simple and inexpensive means to increase the production of commercially important disulfide bond-containing proteins. Because Ero1 may be recombinantly expressed in combination with a commercial protein of interest or may be used as an isolated and purified reagent, the present invention enables the enhancement of disulfide bond formation during in vivo commercial protein production or at subsequent in vitro purification steps, or both. Moreover, to further maximize disulfide bond formation, Ero1 proteins may be used in conjunction with other disulfide bond-forming enzymes, such as PDI proteins. Proper formation of disulfide bonds results in the production of batches of recombinant proteins exhibiting higher yields of properly folded products; this maximizes protein activity and minimizes the presence of species capable of triggering immunological side effects.

Other features and advantages of the invention will be apparent from the following detailed description thereof, and from the claims.

BRIEF DESCRIPTION OF THE DRAWINGS

FIG. 1A is the nucleic acid sequence of the coding strand of the S. cerevisiae Ero1 DNA (SEQ ID NO: 1) shown in the 5' to 3' direction.

FIG. 1B is the amino acid sequence of the *S. cerevisiae* Ero1 polypeptide (SEQ ID NO: 2) shown in the amino-terminal to carboxy-terminal direction.

FIG. 2B shows the results of Gas1p immunoprecipitation at 10, 30, and 60 minutes after initiation of the chase. A sec6 mutant (CKY560) was additionally used to show prevention of degradation of mature Gas1p at the cell surface. The precursor (ER) and mature (Golgi) forms of Gas1p are as indicated. In FIG. 2C, cells carrying pNV31 (a pTPI1-SUC2 fusion) were labeled for 10 minutes and then converted to spheroplasts for the detection of invertase. Invertase was then immunoprecipitated from spheroplasts (int) and supernatant (ex) fractions. The positions of the core-glycosylated ER form and the mature Golgi and secreted forms of invertase are as indicated.

FIG. 3A shows nonreducing and reducing gels demonstrating that in an ero1-1 mutant incubated at 37° C., the p1 form of CPY comigrates with the reduced p1 form of CPY. FIG. 3B shows that in an ero1-1 mutant incubated at 37° C., the p1 form of CPY has free thiols that react with acetamido-4'-maleimidylstilbene-2,2'-disulfonate (AMS).

FIG. 5A shows an autoradiograph of pulse-labeled Ero1p immuno-precipitates treated with 5 mM DTT or 10 μg/ml tunicamycin prior to labeling. FIG. 5B shows the induction of the unfolded protein response (UPR) (as measured by β-galactosidase activity) by ero1-1 cultures at 37° C., or by tunicamycin-treated wild-type cultures at 37° C.

FIG. 8A is a schematic diagram of the Ero1 protein. The signal sequence peptide is shown in black at the N-terminus, and the four regions of high sequence conservation across species are shown in black. The eight predicted N-linked glycosylation acceptor sites (i.e., Asn X Ser/Thr sites) are as indicated.

FIG. 8B is a sequence alignment showing the comparison of the four regions of high sequence conservation in Ero1 with related Ero1 sequences. The species of origin and accession numbers for the sequences are: Sc, *Saccharomyces cerevisiae* (GenBank Accession No.: Z50178); Sp, *Schizosaccharomyces pombe* (GenBank Accession No.: X61926); Tb, *Trypanosoma brucei* (GenBank Accession No.: X60951); Bm, *Brugia malayi* (GenBank Accession No.: AA509062); Dm, *Drosophila melanogaster* (GenBank Accession No.: AA202720); At, *Arabidopsis thaliana* (GenBank Accession No.: T45661); and Hs, *Homo sapiens* (GenBank Accession Nos.: R07093, AA186803, R50884, and AA033538).

FIG. 9 is a table listing the yeast strains used herein.

FIG. 10 is the consensus nucleic acid (SEQ ID NO: 28) and amino acid (SEQ ID NO: 29) sequence for a mammalian ERO1 cDNA molecule.

DETAILED DESCRIPTION

Figure 2A:
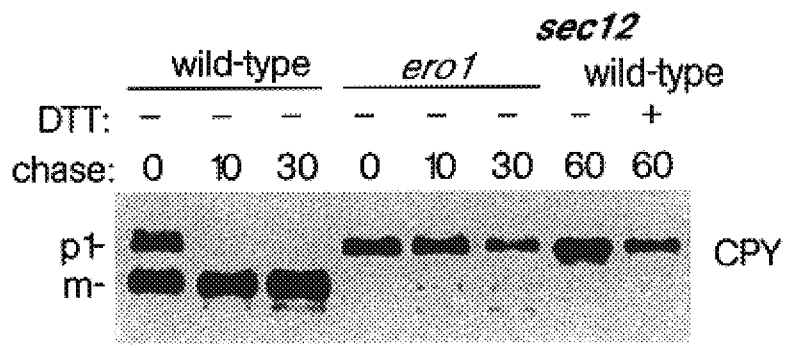
FIGS. 2A, 2B, and 2C are autoradiographs showing that the ero1-1 mutation causes a defect in ER to Golgi transport for a subset of proteins, as compared to the sec12 mutation, which unilaterally blocks ER to Golgi transport. Wild-type (CKY10), ero1-1 (CKY559) and sec12 (CKY39) strains were grown at 24° C., and then shifted to 37° C. Upon shifting to the higher temperature, the strains were pulse labeled with [$^{35}$S] methionine and cysteine for 7 minutes, followed by a chase with an excess of unlabeled methionine and cysteine. The effect of DTT was tested by addition of 5 mM DTT to the cultures 10 minutes before labeling. Protein immunoprecipitated from labeled extracts was resolved by SDS-PAGE. Shown in FIG. 2A are the results of carboxypeptidase Y (CPY) immunoprecipitation at 10, 30, and 60 minutes after initiation of the chase. The p1 (ER) and m (vacuole) forms of the CPY protein are as indicated.

Described below is a novel protein initially isolated from yeast, and termed "Ero1," which is involved in catalyzing the proper formation of disulfide bonds and which may work together for this purpose with another enzyme, PDI, in eukaryotic cells. As described in more detail below, the Ero1 gene was discovered in a screen for new mutations that affected protein secretion in *S. cerevisiae*, and its protein product was subsequently found to be a luminal ER protein essential for disulfide bond formation in the ER. Ero1 appears to be present in many, if not all, eukaryotic cells, since genes homologous to Ero1 exist in other microorganisms (for example, *S. pombe* and *T. brucei*), in plants (*A. thaliana*), and in humans. Ero1 is unique in its ability to vary the oxidizing potential of the ER. In particular, as shown herein, increasing the level of Ero1 increases the oxidizing potential of the ER, and decreasing the level of Ero1 decreases the oxidizing potential of the ER.

Because Ero1 proteins are essential for proper disulfide bond formation, these proteins are useful for catalyzing disulfide bond formation and may be used, if desired, in conjunction with PDI. Ero1 catalysis of disulfide bond formation may be carried out either in vivo or in vitro.

The following examples are included for the purpose of illustrating, and not limiting, the invention.

Identification of Yeast Ero1

To isolate new secretion genes, a collection of 1200 temperature-sensitive S. cerevisiae mutants (Hartwell et al., Genetics 74:267, 1973) was screened for defects in protein transport from the ER. To conduct the screen, each mutant was analyzed by Western blotting analysis for the presence of the ER-retained form of carboxypeptidase Y (CPY). The results of this screen yielded several mutants that displayed defects in ER to Golgi transport that complemented all readily available secretion mutants. One of these new mutations, Ero1, failed to grow above 35° C. and exhibited a complete block in the maturation of the ER form of CPY at these elevated temperatures. In tetrad analysis of backcrosses to wild-type strains, the CPY transport defect and temperature sensitivity cosegregated in 2:2 fashion, indicating that both traits were the result of a single nuclear mutation, which we initially designated "sec81-1," and which we now designate "Ero1."

A library of S. cerevisiae genomic DNA in the centromere vector YCp50 (Rose et al., Cell 57: 1211–1221, 1989) was screened for plasmids that could rescue the temperature sensitivity of ero1-1. In a screen of 20,000 clones, one was identified that complemented both the temperature sensitivity and secretion defects of Ero1. DNA sequencing showed that this clone was derived from the left end of chromosome XIII. Tests of subclones of this region identified the open reading frame YML130c as the complementing gene. An integrating vector with URA3 as a selectable marker was integrated at the YML130c locus by homologous recombination, and, in a cross to an ero1-1 mutant, the URA3 marker was found to be completely linked to temperature sensitivity identifying YML130c as the Ero1 gene.

A chromosomal deletion of Ero1 was constructed in a diploid strain by one-step gene replacement with a DNA segment with the entire coding sequence of Ero1 replaced with the LEU2 gene. Sporulation of this diploid at 25° C. gave only tetrads with two viable spores, neither of which carried the LEU2 marker. Thus, as expected given the existence of the temperature sensitive ero1-1 mutation, the Ero1 gene was essential for yeast viability. The nucleotide sequence of the coding strand of the Ero1 DNA (SEQ ID NO: 1) is shown in FIG. 1A.

The Ero1 gene encodes a protein with a predicted molecular weight of 56 kD. Overall, the amino acid sequence (SEQ ID NO: 2), which is shown in FIG. 1B, is quite hydrophilic. However, the amino terminus appears to be sufficiently hydrophobic to encode a signal sequence. Searches of GenBank identified proteins with similar sequences to Ero1 in other eukaryotic organisms. These organisms included microorganisms (e.g., S. pombe and T. brucei), plants (e.g., A. thalian), and mammals (e.g., humans). Shown in FIG. 8A is a schematic diagram of Ero1. The four regions of high sequence conservation to Ero1 proteins found in other species are shown in gray, while the N-terminal signal sequence peptide fragment is shown in black. Also in FIG. 8A are indicated the eight predicted N-linked glycosylation addition sites (i.e., the sites with the sequence Asn X Ser/Thr).

Shown in FIG. 8B is a comparison of the regions 1–4 depicted in FIG. 8A aligned with translations of all of the sequences related to Ero1 found in other eurkaryotes. Of particular note are the conserved regions corresponding to amino acids 164–209 (Region 2 in FIG. 8A) and 325–375 (Region 4 in FIG. 8A) of Ero1, where more than 70% of the residues are identical between species.

Ero1 is Required for Disulfide Bond Formation

Figure 2B:
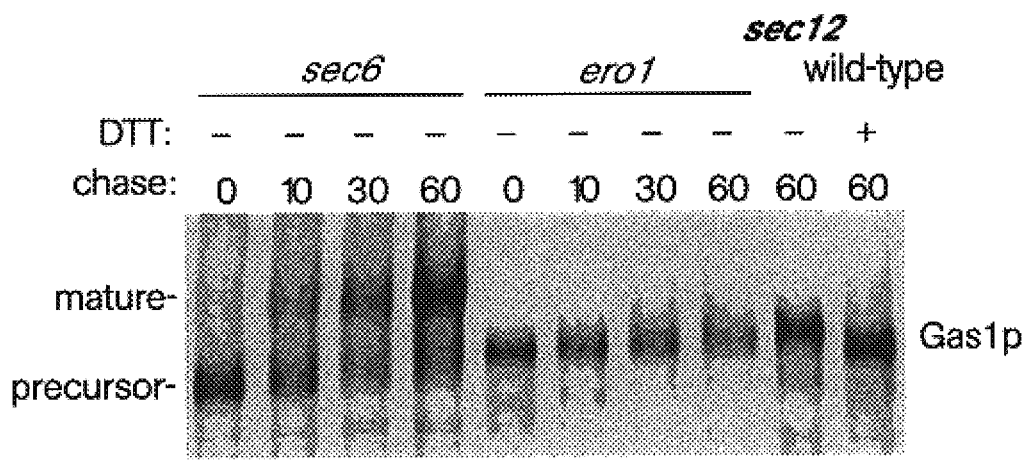
Figure 2C:
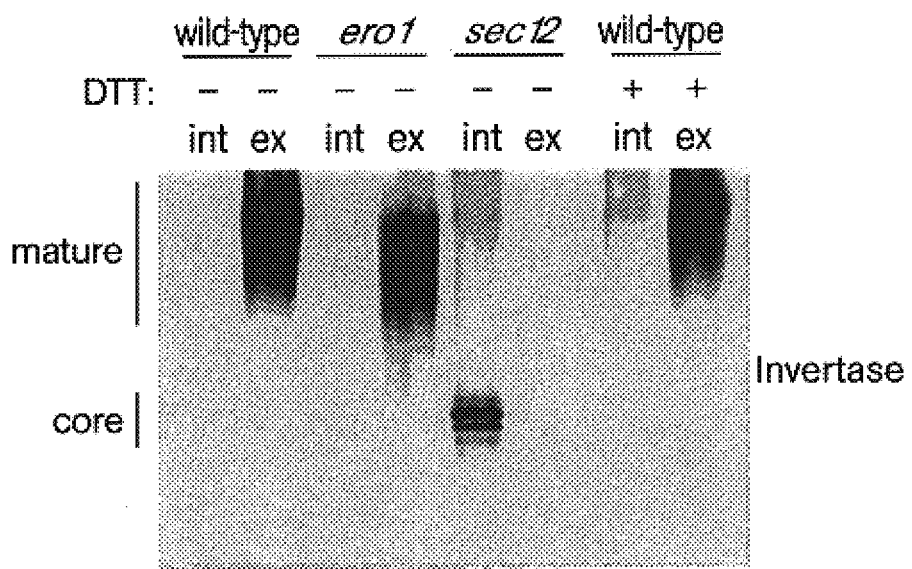

Initially, the ero1-1 mutation appeared to have a phenotype similar to that of SEC gene mutations that are blocked in ER to Golgi transport. However, tests of different secretory proteins revealed that ero1-1 blocked the transport of some secretory proteins but not others. In a pulse-chase experiment designed to follow the maturation of CPY, an ero1-1 mutant at the restrictive temperature of 37° C. exhibited a complete block throughout the duration of a 60 minute chase in the conversion of CPY from the ER form (p1) to the Golgi form and finally, to the vacuolar form (m) of the protein. In a wild-type strain under the same conditions, conversion of the CPY p1 form to the m form occurred in less than 10 minutes (FIG. 2A). In contrast, transport of the secretory protein invertase from the core-glycosolated ER form to the mature secreted form occurred rapidly for both wild type and ero1-1 strains at 37° C. (FIG. 2C).

This finding demonstrated that the ero1-1 mutation did not interfere with the function of COPII transport vesicles, which are responsible for the transport of both invertase and CPY from the ER. Rather, the ERO1 mutations appeared to selectively impede the ability of CPY to exit the ER. In view of this result, it appeared likely that the ero1-1 mutation might interfere with disulfide bond formation in the ER. In particular, CPY requires disulfide bond formation in order to exit the ER, whereas invertase does not. When yeast cells are exposed to the reducing agent, DTT, disulfide bonds do not properly form in CPY, and consequently the incorrectly folded protein fails to be transported from the ER. Invertase, in contrast, can fold properly in a reducing environment, as shown by the formation of an enzymatically active cytosolic form of the enzyme and by the ability of invertase to be secreted rapidly even in the presence of DTT. We reproduced these observations, showing that, in wild-type strains exposed to 5 mM DTT in the growth medium, ER transport of CPY, but not invertase, was blocked (FIGS. 2A and 2C).

In addition, we tested the effect of ero1-1 on the transport of the GPI-linked cell surface protein Gas1p. The conversion of Gas1p from its ER-form (120 kD) to its cell-surface form (125 kD) can be detected as an increase in molecular weight. In our experiments, we found that, in wild-type cells, Gas1p maturation from the ER form was blocked by addition of DTT to the growth medium (FIG. 2B). This finding suggested that proper folding and exit of Gas1p from the ER depended upon disulfide bond formation between cysteine residues in the luminal domain of Gas1p. In an ero1-1 mutant at 38° C., Gas1p remained in the PR form, co-migrating with a form of the protein produced in an PR to Golgi transport mutant sec12-4 (FIG. 2B). Thus, the Ero1 mutant exhibited a similar effect on secretory protein exit from the ER as did treatment of wild-type cells with DTT, suggesting that Ero1 played a role in oxidative protein folding in the ER.

Figure 3A:
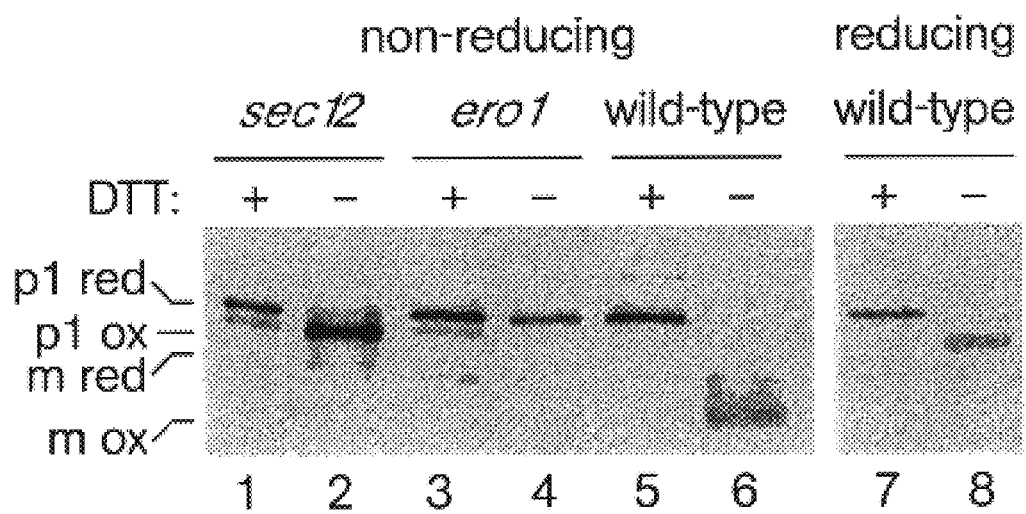
FIGS. 3A and 3B are autoradiographs demonstrating that the ero1-1 mutation causes a defect in disulfide bond formation in CPY.

To examine disulfide bond formation in the ER, the redox state of CPY was determined in Ero1 mutants. On nonreducing SDS gels, reduced CPY can be resolved from properly folded, oxidized CPY by a difference in mobility. CPY isolated from an ero1-1 mutant on a nonreducing gel comigrated with reduced CPY produced by treatment of wild-type with DTT (FIG. 3A). Both forms of CPY migrated more slowly than CPY produced in a sec12 mutant where CPY should be properly oxidized and folded but withheld in the ER where it remains in the p1 form (FIG. 3A, lane 2).

Figure 3B:
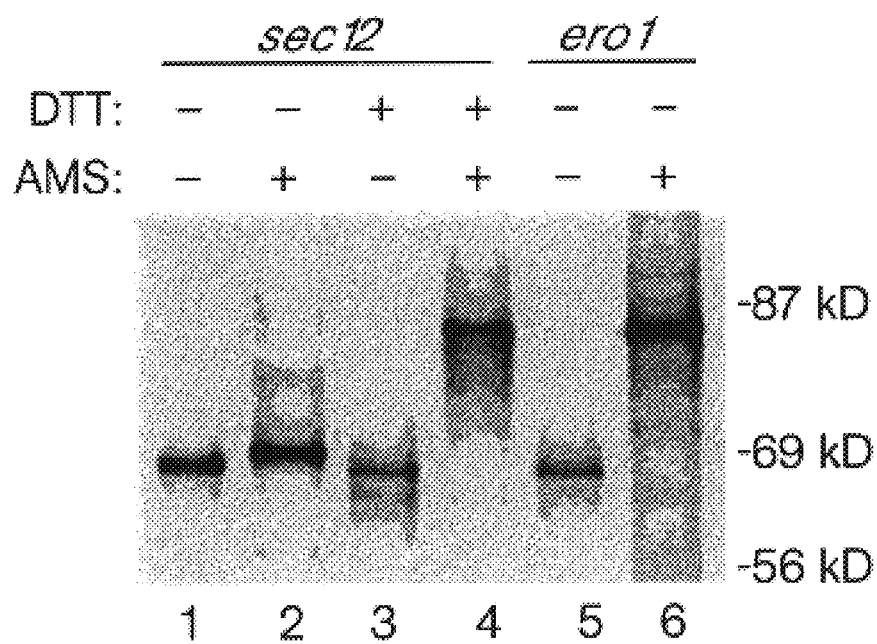

As an independent assay for disulfide bond formation in CPY, we evaluated reactivity of p1 CPY with the thiol-modifying reagent AMS. The maleimide moiety of AMS reacts with cystine thiols on proteins, increasing the molecular weight of the modified protein by approximately 0.5 kb for each AMS residue added. When Ero1 mutant cells were lysed in the presence of AMS, the apparent molecular weight of CPY increased by 5 kD, consistent with the addition of 10 AMS residues (FIG. 3B). In control experiments, p1 CPY prepared from a sec12 mutant was not detectably modified by AMS, whereas p1 CPY prepared from the same cells that had been treated with 5 mM DTT appeared to be fully modified by AMS. Together, these results indicated that disulfide bonds did not form in CPY expressed in the Ero1 mutant at its restrictive temperature. The secretion block in Ero1 mutants could thus be explained as a consequence of this defect in oxidative protein folding.

Ero1p is a Stress-Induced Luminal ER Protein

Figure 4A:
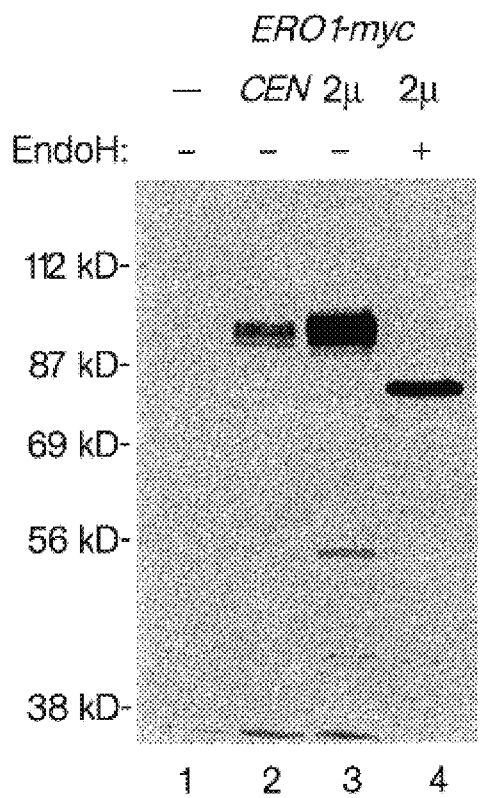
FIG. 4A is an autoradiograph of pulse-chase labeled Ero1p-myc showing that the 96 kD Ero1p-myc protein expressed at high levels from a high copy number plasmid (lane 3) is reduced to 81 kD following treatment with EndoH (lane 4), indicating that Ero1p is an N-linked glycoprotein.

To detect the Ero1 gene product, we placed a myc epitope at the carboxy terminus of the Ero1 protein coding sequence. ERO1-myc complemented the ero1-Δ strain, showing that the modified protein was functional. Antibody to the myc epitope recognized a protein of 96 kD from cells expressing ERO1-myc from a centromere plasmid (FIG. 4A, lane 2). The abundance of Ero1p-myc was greater in cells expressing ERO1-myc from a high copy 2μ plasmid (FIG. 4A, lane 3). Treatment of extracts with endoglycosidase H (Endo H) reduced the apparent molecular weight of Ero1p-myc to 81 kD (FIG. 4A, lane 4); the shift in molecular weight after removal of N-linked carbohydrate chains was consistent with the modification of all eight predicted Asn X Ser/Thr acceptor sites in Ero1p. These experiments indicated that Ero1p was an N-linked glycoprotein, and that the hydrophobic amino terminal sequence was likely a signal sequence.

Figure 4B:
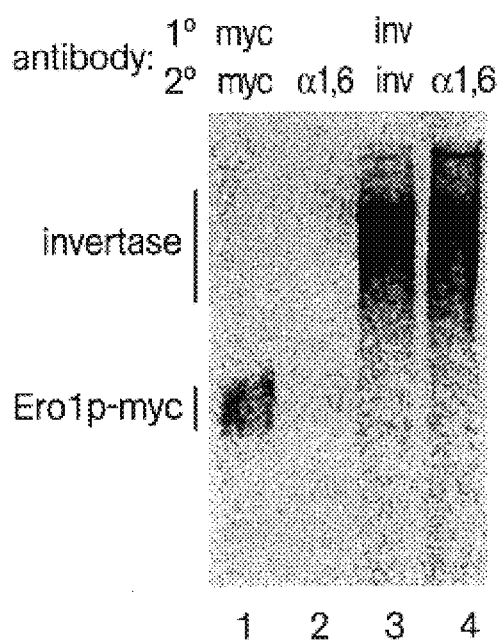
FIG. 4B is an autoradiograph of pulse-chase labeled Ero1p-myc and invertase immunoprecipitates (with anti-myc and anti-invertase antibodies, respectively), followed by a second immunoprecipitation with an anti-α1, 6 mannose residue antibody. Unlike invertase, Ero1p-myc could not be reimmunoprecipitated with the anti-α1, 6 mannose residue antibody (compare lanes 2 and 4), indicating that most of the Ero1p protein resided in the endoplasmic reticulum.

In addition, Ero1p-myc could not be re-immunoprecipitated with antibody against α1, 6 mannose residues, a modification specific for the cis-Golgi, showing that most of the protein resided in the ER (FIG. 4B). The ERO1 sequence did not contain obvious transmembrane sequences or retention motifs (for example, KKXX or HDEL) raising the question of how the protein was retained in the ER. We found that all of the Ero1p was included in the membrane fractions of cell extracts and could be solubilized by 1% Triton X-100. However, Ero1p-myc was not extracted by 0.5 M NaCl, 2.5 M urea, or 0.1 M carbonate (pH 11.5), conditions that release the luminal protein Kar2p from the membrane. These observations indicated that Ero1p-myc was tightly bound to the inner face of the ER membrane.

Figure 5A:
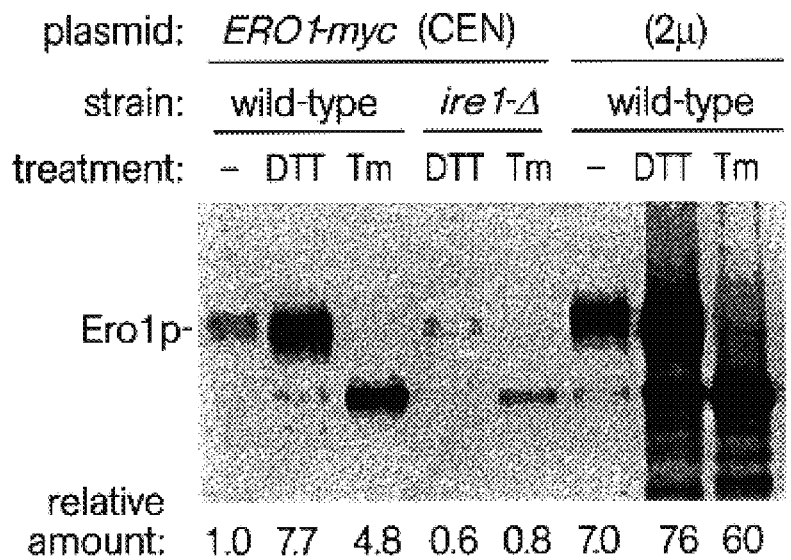
FIGS. 5A and 5B are an autoradiograph and a graph, respectively, showing the regulation of Ero1.

In yeast, ER chaperones are regulated by the unfolded protein response (UPR). For example, KAR2 and PDI1 are transcriptionally induced in response to agents that disrupt the maturation of proteins in the ER, such as tunicamycin and DTT. Likewise, Ero1p-myc expression was induced 20-fold by treatment of cells with 5 mM DTT and 10-fold by treatment with 10 μg/ml tunicamycin (FIG. 5A). In cells with ERO1-myc on a multi-copy plasmid, Ero1p-myc expression was increased further upon treatment with DTT or tunicamycin (FIG. 5A, lanes 2μ lanes). Induction of the UPR requires the ER transmembrane kinase encoded by the IRE1 gene. In our experiments, cells with a chromosomal deletion of IRE1 failed to induce expression of ERO1 in response to either DTT or tunicamycin (FIG. 5A, ire1Δ lanes). Thus, ERO1 appeared to be regulated by the established UPR pathway.

Figure 5B:
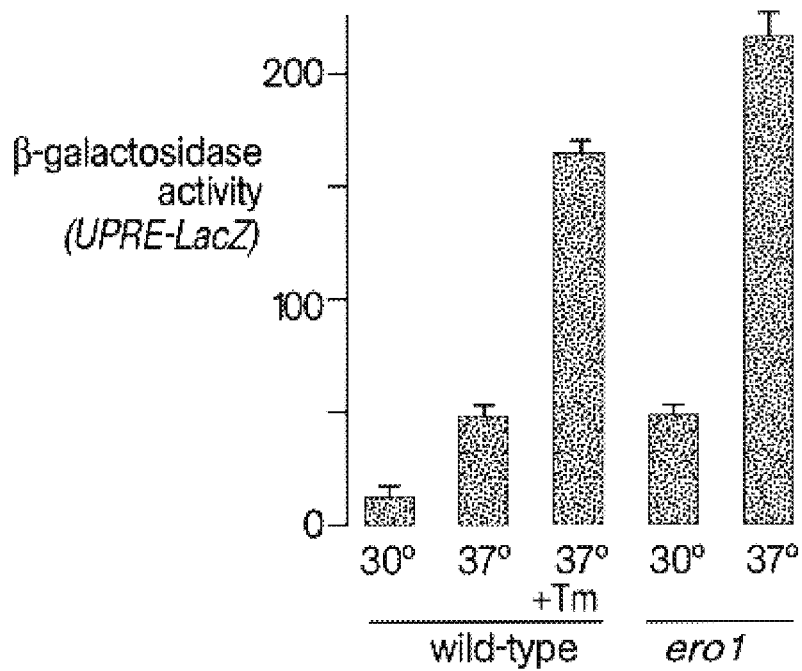

We next determined if loss of ERO1 function could induce the UPR. An Ero1 mutant (i.e., ero1-1) incubated at either 30° C. (permissive) or 37° C. (restrictive) induced expression of a UPRE-LacZ reporter about 5-fold as compared to an isogenic wild-type strain under the same conditions (FIG. 5B). A similar induction of the UPRE-LacZ reporter was observed for wild type cells treated with 2.5 μg/ml tunicamycin at 37° C. The compensatory induction of the UPR in ero1-1 mutants was apparently necessary for cell survival, since in genetic crosses ero1-1, ire1Δ double mutant segregants were inviable. Both the induction of ERO1 with the UPR and the induction of the UPR in Ero1 mutants supported the role of ERO1 in oxidative protein folding in the ER.

Interaction Between ERO1 and Exogenous Reductants and Oxidants

Figure 6A:
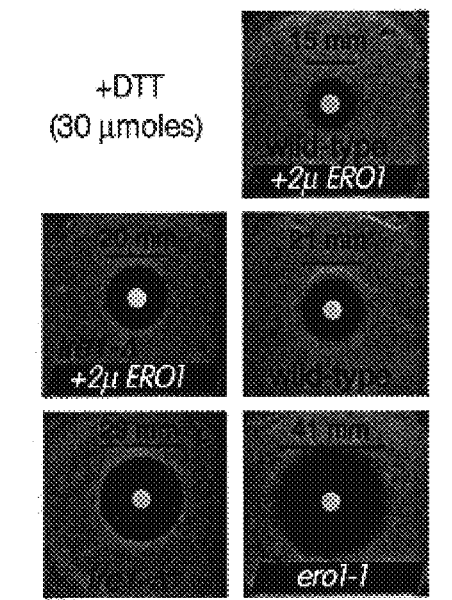
FIG. 6A is a photograph of plates of cells, as indicated, cultured in the presence of a central filter disk containing 30 μmoles DTT for 3 days at 30° C.
Figure 6B:
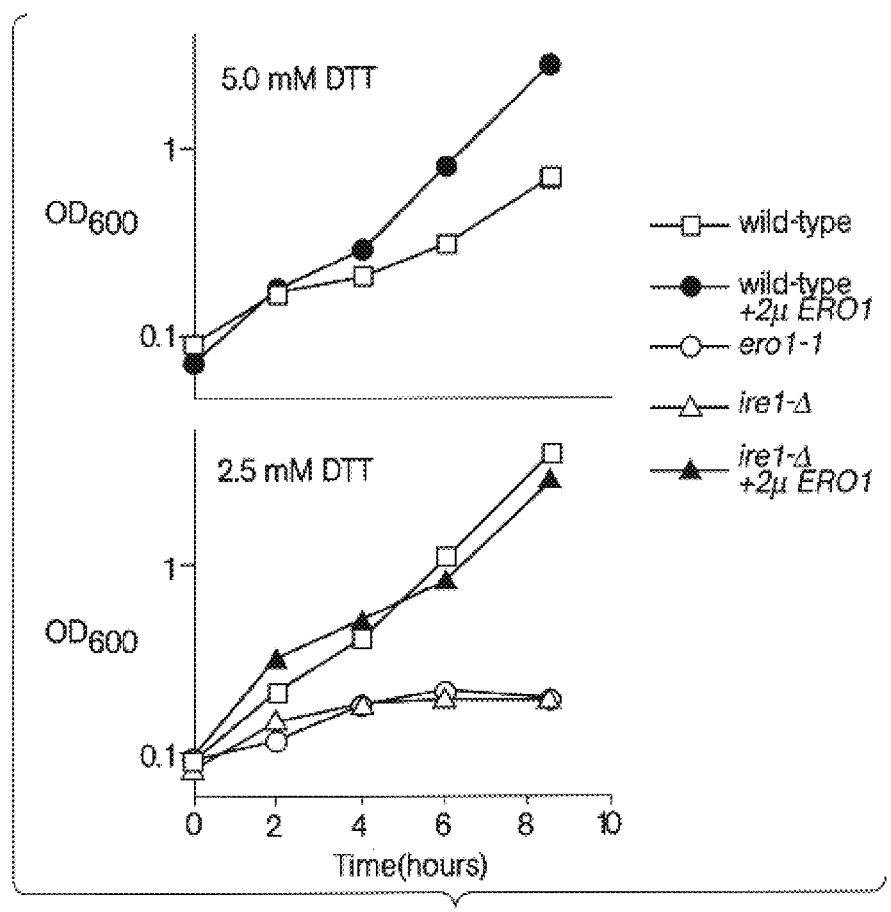
FIG. 6B are two graphs showing the growth rate (as measured by $OD_{600}$) of indicated cells in the presence of 5 mM DTT (upper graph), or 2.5 mM DTT (lower graph).

A mutant with reduced capacity to oxidize protein thiols would be expected to exhibit heightened sensitivity to membrane permeant reducing reagents. We tested the sensitivity of yeast strains to a gradient of DTT concentrations by placing a filter disk containing 30 μmoles of DTT on top of a lawn of yeast cells. At the permissive temperature of 30° C., an ero1-1 strain was particularly sensitive to DTT, giving a halo of inviable cells of approximately 4 cm around the disk, whereas an isogenic wild-type strain had a halo of approximately 2 cm in diameter (FIG. 6A). The sensitivity of ero1-1 mutants to DTT was corroborated by growth assays in liquid culture. Addition of 2.5 mM DTT to YPD slowed the growth of wild-type, but completely prevented the growth of the ero1 mutant (FIG. 6B). The increased sensitivity of the ero1-1 mutant to DTT at 30° C. indicated that, even at permissive growth temperature, this mutant had a reduced capacity to generate an oxidizing environment in the ER, and this result was consistent with the finding that an ER stress response was induced in ero1-1 at 30° C.

We also tested the possibility that increased dosage of ERO1 could render cells more resistant to DTT. As indicated by the halo assay, a strain overexpressing ERO1 from a high copy plasmid (2μ ERO1) exhibited increased resistance to DTT, producing a halo that was 1.5 cm in diameter (as compared to a halo of 2 cm for wild-type) (FIG. 6A). In corresponding assays in liquid culture, wild type cells were sensitive to 5 mM DTT in YPD, whereas the strain overexpressing ERO1 was capable of growth in this medium (FIG. 6B).

We also carried out tests for sensitivity to DTT in strains carrying a chromosomal deletion of the IRE1 gene. We knew that exposure of yeast cells to DTT induced the UPR, which in turn increased expression of a number of ER proteins, any of which could contribute to the cell's resistance to DTT. The advantage of using an ire1-Δ strain background was the elimination of UPR induction, allowing the singular contribution of ERO1 to DTT resistance to be assessed. As was shown previously (Cox et al., Cell 87:391–404, 1996), deletion of IRE1 increased sensitivity to DTT. Consistent with this result, the halo for an ire1-Δ mutant (ire-Δ) was approximately 3 cm, compared to an approximately 2 cm halo for the corresponding wild-type strain (FIG. 6A). Addition of ERO1 on a high copy plasmid to the ire1-Δ strain (ire-Δ 2μ ERO1) increased resistance to DTT to about the level of wild type cells, as indicated by both the halo assay and growth in liquid medium supplemented with DTT (FIGS. 6A and 6B). From these experiments, it appeared that Ero1p was the limiting component that allowed cells to cope with the stress of lethal doses of DTT, and that the natural resistance of cells to DTT that is afforded by induction of the UPR could be accounted for by an increase in ERO1 expression.

Figure 6C:
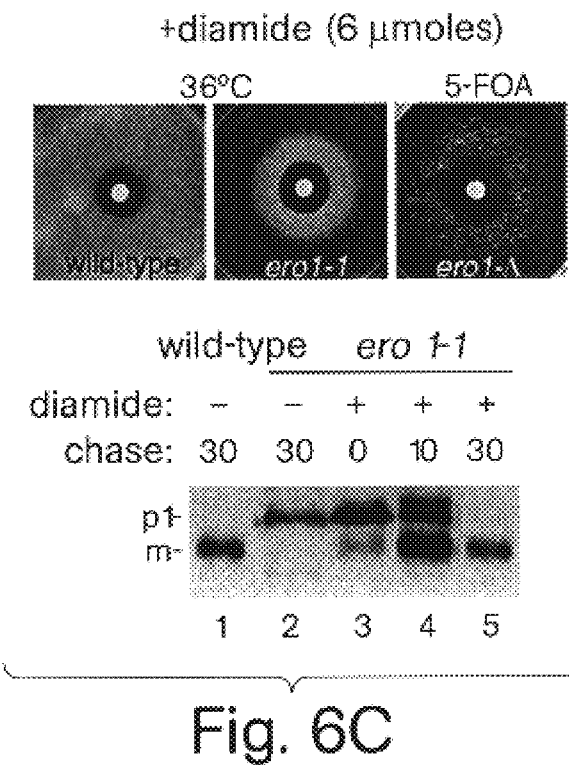
FIG. 6C is a photograph of plates (upper panel) of indicated cells treated for three days with 6 μmoles of diamide at 36° C., and an autoradiograph (lower panel) of Ero1p immunoprecipitates from diamide-treated indicated cells.
Figure 7A:
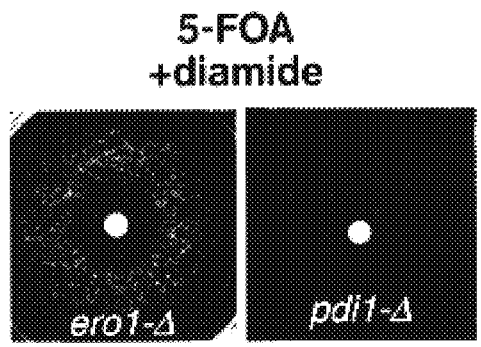
FIG. 7A is a photograph of plates of ERO1-Δ (CKY563) and PDI1-Δ (CKY564) mutant cells cultured on 5-fluoro-orotic acid (5-FOA) plates in the presence of a central filter disk containing 6 μmoles diamide for 7 days at 2520 C.

Given that the ero1-1 mutant increased the sensitivity of cells to exogenous reductant, we explored the possibility that the lethality of Ero1 mutations could be compensated for by an exogenous oxidant. The diazine compound diamide drives formation of disulfide bonds and, when added to the growth medium, enters living cells. We tested the ability of diamide to rescue an ero1-1 mutation by placing 6 μmoles of diamide on a filter disk onto a lawn of ero1-1 cells plated at the restrictive temperature of 37° C. The presence of diamide supported a ring of growth of the ero1-1 mutant, showing that the lethal effect of the mutant was reversed by an appropriate concentration of the oxidant (FIG. 6C). The inner diameter of the ring of growth indicated sensitivity of cells to high concentrations of diamide, which was approximately the same for ero1-1 and wild-type cells (FIG. 6C, upper panel). To show that diamide could restore the capacity for oxidative folding to Ero1 mutants, we demonstrated that CPY was transported to the vacuole normally when the ero1-1 mutant cultured at restrictive temperature was exposed to 5 mM diamide in the growth medium (FIG. 6C, lower panel). Finally we tested the ability of diamide to restore growth to an Ero1 null mutant. A strain containing a chromosomal ero1-Δ covered by a functional copy of ERO1 on a URA3 bearing plasmid, was grown without selection in medium containing 5 mM diamide to allow loss of the plasmid. To select for cells that had lost the plasmid but could grow because of an appropriate concentration of exogenous diamide, the culture was plated on medium containing 5-FOA, to select against Ura3+, with 6 μmoles of diamide in a filter disk placed on the lawn to provide a gradient. A ring of clones around the filter disk indicated that the ero1-Δ strain could be suppressed by an appropriate concentration of diamide (FIG. 7A). We verified that the colonies growing on this plate carried only the ero1-Δ allele by showing that they were ura3⁻ and were dependant on diamide for growth.

Figure 6D:
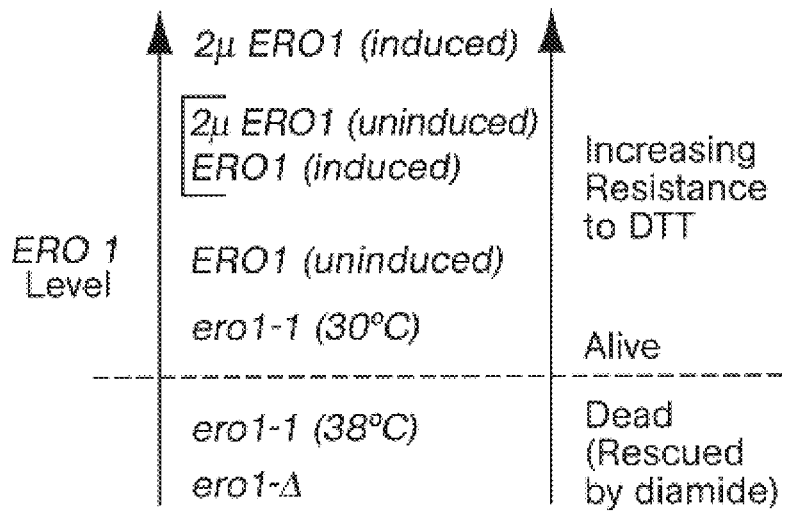
FIG. 6D is a diagram summarizing the response of cells with either increased or decreased levels of Ero1 function to either DTT or diamide.

The diagram in FIG. 6D summarizes the response of cells with either increased or decreased levels of ERO1 function to either exogenous reductant or oxidant. All of the results supported the view that the level of ERO1 function set the redox potential of the ER: increased ERO1 function appeared to make the ER more oxidizing, leading to increased resistance to DTT, whereas reduced ERO1 function appeared to render the ER insufficiently oxidizing, a condition that could be corrected by exogenous diamide.

ERO1 and PDI1 Perform Distinct Functions

Yeast contains a family of genes, related to PDI, that are known to be involved in the proper formation of disulfide bonds. These include: PDI1, EUG1 (Tachibana and Stevens, Mol. Cell Biol. 12:4601, 1992), and MPD1 (an uncharacterized open reading frame which encodes a membrane protein with a PDI-like sequence in what is predicted to be a luminal domain). Although the sequence of ERO1 did not have a thioredoxin motif, common to all PDI-like proteins, we were interested in exploring the functional relationship of Ero1 to members of the PDI family.

We first tested to see if a reduction in PDI1 function would exacerbate the growth defect of an ero1-1 mutation. A useful form of PDI1 for such tests is an allele with a deletion of the carboxy terminal HDEL sequence. Cells carrying this PDI-ΔHDEL are viable but have low intracellular levels of Pdi1p because Pdi1p that has escaped the ER cannot be retrieved. In crosses between ero1-1 and pdi-ΔHDEL mutants, spore inviability at 24° C. segregated as a two-gene trait (that is, dead:viable spore clones showed 2:2, 1:3, and 0:4 segregation patterns). Genotypic analysis of the surviving sister spore clones revealed that the inviable spores were always ero1-1 pdi-ΔHDEL double mutants. This synthetic lethal interaction between the ERO1 and PDI1 genes provided evidence that both genes were involved in the same process.

This synthetic lethal interaction was not general for all ER chaperones since double mutants of ero1 and kar2-ΔHDEL were viable and had a threshold restrictive temperature that was the same as that for the ero1-1 single mutant.

Figure 7B:
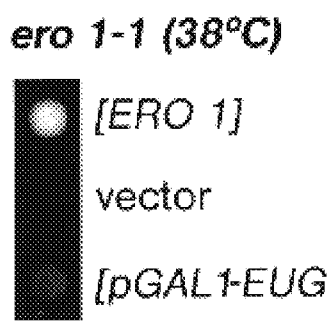
FIG. 7B is a photograph of ero1-1 mutants (strain CKY559) transformed with the indicated vectors cultured on a YPD plate at 38° C.
Figure 7C:
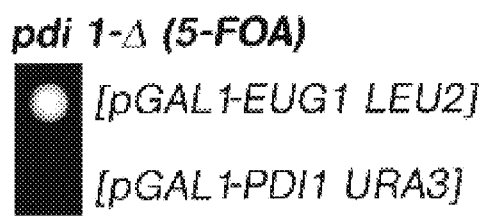
FIG. 7C is a photograph of PDI1-Δ (CKY564) mutants transformed with the indicated vectors cultured on 5-fluoro-orotic acid (5-FOA) plates for 4 days at 30° C.

Functional redundancy between members of the yeast PDI family has been demonstrated by the ability of over-expression of either EUG1 or MPD1 to suppress the lethality of a chromosomal deletion of PDI1 (Tachibana and Stevens, supra). In our experiments, we introduced a plasmid carrying EUG1 expressed from the GAL1 promoter (pCT44) into an ero1-1 mutant. Expression of EUG1 on galactose medium could not suppress the temperature sensitivity of ero1-1 (FIG. 7B), but in a control experiment, pCT44 could suppress the lethality of pdi1-Δ (FIG. 7C). Similarly, we found that PDI1 expressed from the GAL1 promoter (pCT37) did not alter the temperature sensitivity of an ero1-1 mutant.

Methods

The methods used for carrying out the isolation and characterization of Ero1 were as follows.

Plasmid Construction pAF9, isolated from the YCp50 library, carries the ERO1 gene on a 6.5 kb genomic insert. For integrative mapping of the cloned gene, plasmid pAF23, which carries a 2.6 kb SalI-XbaI fragment from pAF9 inserted into the integrating vector pRS306, was used. An epitope tagged version of Ero1 wag constructed by first introducing a NotI site after the last codon of Ero1 by site directed mutagenesis and then inserting a 128 bp sequence that encodes three tandem copies of the c-myc epitope: EQKLISEEDLN (SEQ ID NO: 11). This segment was reconstructed with the full-length gene (including 1156 bp 5' of the ATG and 394 bp 3' of the stop codon) in vector pRS316 to generate pAF82. Ero1-myc was shown to complement both ero1-1 and ero1-Δ::LEU2. The insert with ERO1-myc from pAF82 was inserted into the following vectors: pRS315 (LEU2) to generate pAF85; pRS306-2μ (2μ URA3) to generate pAF84; and pRS305-2μ (2μ LEU2) to generate pAF89. The UPRE reporter pCF118 carries the 5' region of KAR2 fused to lacZ in a CEN LEU2 vector. pNV31 carries the TPI1 promoter fused to the SUC2 gene in a CEN URA3 vector. pAF92 carries the PDI1 gene isolated by PCR amplification of genomic sequences fused to the pGAL1 promoter in vector pCD43 (CEN URA3). This construct was shown to overproduce Pdi1p by Western blotting with anti-Pdi1p antibody. pCT37 carried a fusion of pGAL1 to PDI1 in a CEN URA3 vector and PCT44 carries a fusion of pGAL1 to EUG1 in YEp351 (2μ LEU2).

Media and Strains

A table listing different S. cerevisiae strains used in this study is provided in FIG. 9. S. cerevisiae cultures were grown and genetically manipulated using techniques as previously described (see, e.g., Kaiser et al., Methods in Yeast Genetics, Cold Spring Harbor Laboratory Press, Cold Spring Harbor, N.Y., 1994). The following medias were used to propagate the yeast cultures: YPD, a rich medium with 2% glucose; YEP, a rich medium to which a specified carbon source was added; SD, a minimal medium (Difco Laboratories Inc., Detroit, Mich.); SC, a minimal medium supplemented with all of the amino acids; and SM, a minimal medium supplemented with adenine plus tryptophan, histidine, arginine, methionine, tyrosine, leucine, isoleucine, lysine, phenylalanine, glutamic acid, aspartic acid, valine, threonine, and serine.

The ero1-1 mutant was identified in a collection of temperature sensitive mutants in the S. cerevisiae strain A364A. The original mutant which was both temperature sensitive and defective in the maturation of CPY was backcrossed 10 times to a wild-type genetic background S288C. In tetrad analysis of the final backcrosses, the CPY transport defect segregated 2:2 and cosegregated with temperature sensitivity. The ero1-1 mutants were viable at 25° C., grow poorly at 33° C., and were dead at 36° C. CKY558 and CKY559 were two of those backcrossed strains. To disrupt the ERO1 gene, a 1.1 kb BglII-HindIII fragment (encoding amino acids 124–500 of Ero1p) was removed from pAF23 and was replaced by the LEU2 gene from pJJ252 (Jones and Prakash, Yeast 6: 363–366, 1990). A 2.8 kb fragment carrying ero1-Δ::LEU2 was liberated from the resulting plasmid pAF25, by digestion with XhoI and NotI. CKY562 was constructed by introduction of this ero1-Δ::LEU2 fragment into the chromosome of a diploid formed by mating CKY8 with CKY10 by transformation and homologous recombination. Sporulation of and tetrad analysis of CKY562 gave 2:2 segregation of lethality where all viable spore clones were Leu-. CKY562 was transformed with pAF82 (ERO1-myc CEN URA3) and on sporulation Leu+ segregants could be isolated, but these depended on pAF82 for viability (no Ura-segregants could be isolated on 5-fluoro-orotic acid plates). A chromosomal deletion of IRE1 was constructed by transformation of CKY10 with the ire1-Δ::URA3 fragment obtained from pCS109A (Shamu and Walter, EMBO J. 15: 3028–3039, 1996). The phenotype of ire1-Δ was verified by the inability of URA+ disruptants to induce LacZ expression from pCF118.

Radiolabeling and Immunoprecipitations

Strains were grown in SD medium containing 2% glucose and auxotrophic supplements to about $1\times10^7$ cells/ml and then were collected by centrifugation and suspended in SD at $1.5\times10^7$ cells/ml. Cell proteins were labeled by addition of 40 μCi of [$^{35}$S] methionine and cysteine (NEN-Dupont) per $2\times10^7$ cells for 7 minutes. The chase was initiated by addition of 0.3 mM methionine, 0.3 mM cysteine, and 1 mM ammonium sulfate, and samples of $2\times10^7$ cells were collected at times after the initiation of chase in 10 mM NaN$_3$. Protein extracts were prepared from cell pellets in 30 ml of 80 mM Tris-HCl pH 6.8, 2% β-mercaptoethanol, 2% SDS, and 1 mM PMSF by heating to 95° C. for 2 minutes followed by vigorous agitation with acid-washed glass beads. Solubilized samples were suspended in 1 ml of IP buffer (50 mM Tris-HCl pH 7.4, 150 mM NaCl, 1% Triton X-100) preadsorbed with fixed Staphlococcus A cells, cleared by centrifugation and then incubated with primary antibody for 2 hours at 25° C. Immune complexes were collected by incubation with Protein A Sepharose (Pharmacia), washed in IP buffer and then solubilized in 20 μl ESB (80 mM Tris-HCl pH 6.8, 100 mM DTT, 1% SDS, 1 mM PMSF, 10% glycerol, 0.1% bromphenol blue). Samples were resolved by SDS-PAGE and were either exposed to X-ray film (Kodak) or were analyzed with a 445si Phosphorimager and ImageQuant Software (Molecular Dynamics, Sunnyvale, Calif.).

In particular cases the protocol was modified. To examine the effect of DTT on protein transport, 5 mM DTT was added to cell cultures 10 minutes before labeling. Temperature sensitive mutants were grown at 25° C. and then were shifted to 37° C. 5 minutes before labeling. We found that Gas1p that had reached the cell surface was sensitive to proteolytic degradation that was not inhibited by our standard cocktail of protease inhibitors. Therefore, for the kinetic analysis of Gas1p maturation, we used a sec6-1 mutant which blocked fusion of post-Golgi secretory vesicles with the plasma membrane, thereby stabilizing the mature form of Gas1p. For detection of intracellular and extracellular invertase (see, e.g., Fy2c), cells were collected in 10 mM NaN$_3$ and then were converted to spheroplasts by incubation in 0.1 M Tris SO$_4$ (pH 9.4) and 50 mM β-mercaptoethanol for 10 minutes followed by incubation in 80 μl of 10 mM Tris HCl pH 7.5, 1.2 M sorbitol, and 50 U of recombinant lyticase for 60 minutes at 30° C. Spheroplast pellet and supernatant fractions were separated by centrifugation at 2,500 rpm in a clinical centrifuge. Each fraction was then suspended in IP buffer and incubated with anti-invertase antibody.

Assay of Disulfide Bond Formation in CPY

Disulfide bond formation in CPY was assayed in two different methods. The first method relied on the fact that properly folded, oxidized CPY migrates more rapidly than reduced CPY on nonreducing SDS PAGE. Wild type (CKY10), ero1-1 (CKY559), and sec12 (CKY39) strains were grown in SD medium at 25° C. then shifted to 38° C. for 20 minutes. To half of the samples 5 mM DTT was added, and incubation was continued for 10 minutes. The cells were then labeled with [$^{35}$S] methionine and cysteine for 30 minutes at 38° C. Labeling was terminated, and free thiols were blocked by placing cells in 10 mM NaN$_3$ and 20 mM N-ethyl maliemide (NEM). Cell pellets were lysed in either 30 μl of 80 mM Tris-HCl pH 6.8, 2% β-mercaptoethanol, 2% SDS, and 1 mM PMSF (reducing) or 30 μl of the same buffer without β-mercaptoethanol (nonreducing). CPY was immunoprecipitated, and samples were suspended in either ESB, or ESB without DTT, and resolved by SDS-PAGE.

In the second method, free protein thiols were modified with AMS, and the extent of modification was detected as a decrease in mobility on SDS-PAGE. Wild type (CKY10), ero1-1 (CKY559), and sec12 (CKY39) strains were grown in SD medium at 25° C., shifted to 38° C. for 10 minutes, and then labeled with [$^{35}$] methionine and cysteine for 30 minutes at 38° C. To half of the samples 5 mM DTT was added 10 minutes before labeling. Cell pellets were lysed in 30 μl of 80 mM Tris-HCl pH 6.8, 1% SDS, 1 mM PMSF, and 20 mM AMS, and were incubated in this buffer for 30 minutes at 25° C. CPY was immunoprecipitated and resolved on nonreducing gels as described above.

Detection and Quantitation of Ero1p

To detect Ero1p, strains expressing a myc-tagged version of the gene (ER)1-myc) were grown in SD medium at 30° C., and were then pulse labeled with [$^{35}$S] methionine and cysteine for 30 minutes. Cell pellets were lysed in 30 μl of 80 mM Tris-HCl pH 6.8, 20 mM β-mercaptoethanol, 1% SDS, 1 mM PMSF, and diluted into 1 ml of IP buffer. Ero1p-myc was immunoprecipitated with 9E10 monoclonal anti-myc antibody, suspended in ESB, and resolved by SDS-PAGE. For endoH digestion samples were diluted four-fold in 50 mM sodium citrate pH 5.5 with 100 units of endoH (New England Biolabs). To test induction of Ero1 expression by the UPR, either 5 mM DTT or 10 μg/ml of tunicamycin (Sigma) was added to the cultures 10 minutes before labeling. Quantitation of Ero1 induction was analyzed with a phosphorimager.

To test for the Golgi-specific α 1,6 mannose modification on Ero1p, immunoprecipitates of Ero1p-myc were represpitated with anti-α 1,6 mannose antibody. As a control to demonstrate the efficacy of the antibody, mature invertase (isolated from a sec6 mutant) was precipitated with anti-invertase antibody and then reprecipitated with anti-α 1,6 mannose antibody.

Induction of the Unfolded Protein Response

CKY10 (ura3-52) and CKY559 (ero1-1 ura3-52) were transformed with the plasmid pCF118, which carries a kar2-lacZ fusion. Transformants were grown in SC medium without leucine at 25° C. to a density of 1×10⁷ cells/ml. The temperature was then shifted to either 30° C. or 37° C., or 2.5 μg/ml tunicamycin was added, and incubation was continued for 2.5 hours. Cells were then permeabilized by treatment with chloroform and SDS, and β-galactosidase activity was assayed by standard techniques. Enzymatic activities were normalized to $OD_{600}$. Two transformants were assayed, and the experiment was repeated twice.

To test for synthetic-lethality between ero1-1 and pdi1-ΔHDEL, strains CKY558 and CKY395 were crossed and the resulting tetrads were dissected. Lethality segregated as a two-gene trait on YPD medium at 25° C. (segregation patterns of live: dead of 4:0, 1:3, and 2:2 were seen). The surviving sister spores were tested for ero1-1 (temperature sensitivity) and pdi1-ΔHDEL (Pdi1p secretion into the medium), and their genotypes showed that the dead spores were always double mutants.

Growth Tests in the Presence of DTT or Diamide

To test for sensitivity to DTT, 2×10⁶ cells were plated on YPD medium and 30 μmoles of DTT was placed on top of the lawn in a 6 mm sterile filter disk. Plates were photographed after three days at 30° C. Growth was also tested by measuring the change in $OD_{600}$ with time in YPD medium with either 2.5 mM DTT or 5 mM DTT. To test for rescue by diamide, wild-type (CKY10) or ero1-1 (CKY559) were plated at 3×10⁶ cells/plate and 6 μmoles of diamide was placed on top of the lawn in a 6 mm sterile filter disk. Plates were photographed after three days at 36° C. As negative controls, temperature-sensitive kar2 mutants (kar2-159 and kar2-203) were plated at 33° C., and no growth was detected in the presence of diamide. To test for suppression of ero1-Δ by diamide, the null allele covered by ERO1 genes on URA3 plasmid (CKY563) was grown to saturation in YPD with 0.4 mM diamide to allow loss of the plasmid. Similarly, the plasmid covered pdi-Δ strain (CKY564) was grown in YEP medium with 2% galactose and 0.4 mM diamide. Cultures were plated at 3×10⁶ cells/plate onto SC plates supplemented with 1 mg/ml 5 fluoro-oritic acid and a filter disk with 6 μmoles of diamide. The plates were photographed after seven days at 25° C. The colonies of CKY563 that grew in a ring around the diamide source were shown to be diamide dependent (on replating on a SC plate with 6 μmoles of diamide spotted in the center, they grew only near the source of diamide), and ura3—(they did not grow on SC plates without uracil even in the presence of diamide).

Suppression Tests

To test the ability of overexpression of PDI1 or EUG1 to suppress the temperature sensitivity of ero1-1, CKY559 was transformed with pAF82 (ERO1-myc CEN URA3), pAF92 (pGAL1-PDI1 CEN URA3), pCT44 (pGAL1-EUG1 2μ LEU2), or prs316 (CEN URA3). Purified transformants were grown selectively on SC medium, and then in SC medium with 2% raffinose and 2% galactose to induce pGAL1 expression. Serial dilutions of the cultures were spotted on YEP medium with 2% raffinose and 2% galactose and incubated at 38° C. for three days. To confirm that EUG1 overexpression suppressed the lethality of pdi1-Δ, CKY564 (pdi1-Δ [pGAL1-PDI1 URA3]) and CKY564 with pCT44 were plated on SM medium containing 2% raffinose and 2% galactose and 1 mg/ml 5-FOA. These plates were incubated at 30° C. for four days.

To test for the ability of overexpression of ERO1 to suppress kar2 mutations, CKY222 (kar2-159) and CKY229 (kar2-203) were transformed with pAF84 (ERO1-myc 2μ URA3), and were plated at restrictive temperatures of 30°–38° C. No improvement of growth of the transformed strains was detected over strains transformed with vector only.

Cloning Mammalian Ero1 Sequences

Based on our isolation of novel yeast ERO1 cDNAs, the isolation of mammalian ERO1 nucleic acid sequences, including human ERO1 sequences, is made possible using the sequences described herein and standard techniques. In particular, using all or a portion of a yeast ERO1 sequence, one may readily design oligonucleotide probes, including degenerate oligonucleotide probes (i.e., a mixture of all possible coding sequences for a given amino acid sequence). These oligonucleotides may be based upon the sequence of either strand of the DNA.

Exemplary probes or primers for isolating mammalian ERO1 sequences preferably correspond to conserved blocks of amino acids, for example, conserved Ero1 motifs. Exemplary motifs are as follows, in the N to C direction, using the standard one letter code where (X) is any amino acid, (Ac) is any acidic amino acid, (Ba) is any basic amino acid, and (Hb) is any hydrophobic amino acid:

Ero1 Region 1: LLKSDFFKYFRLDLYKQCSFW (SEQ ID NO: 3);
Ero1 Region 2: AVLIDLTANPERFTGYGGKQAGQIWSTIYQDNC (SEQ ID NO: 4);
Ero1 Region 3: AKDAFYRLVSGFHASIGTHLS (SEQ ID NO: 5);
Ero1 Region 4: LKDEFRSRFKNVTKIMDCVQCDRCRLWGKIQTTG YATALKILF (SEQ ID NO: 6);
Ero1 Region 2A: DL(X)(X)NPE(X)(X)TGY (SEQ ID NO: 7);
Ero1 Region 3A: L(Hb)SGLHASI (SEQ ID NO: 8);
Ero1 Region 4A: (Hb)MDCV(X)C(Ac)(Ba)CR(Hb)WGK (SEQ ID NO: 9); and
Ero1 Region 4B: TALK(Hb)(Hb)F (SEQ ID NO: 10).

Using such motifs, partial or complete mammalian ERO1 genes may be isolated from sequence databases (for example, by the use of standard programs such as Pileup). Examination of the yeast ERO1 sequence, for example, has allowed for the elucidation of the mammalian ERO1 sequence shown in FIG. 10 (SEQ ID NOS: 28 and 29). The nucleotide residues of this sequence were derived from the GenBank sequences listed below in Table I.

TABLE I

Sources for Mammalian Ero1 Consensus Sequence

| Nucleotide Sequence | GenBank Accession No. | Source |
| --- | --- | --- |
| 1–156 | AA305384 | human |
| 157–242 | AI060157 | rat |
|  | AA920983 | mouse |
|  | AA867609 | mouse |
| 243–508 | R07093 | human |
| 509–805 | AA179578 | human |
| 806–900 | R50884 | human |
|  | AA186803 | human |
| 900–1102 | AA021774 | mouse |
|  | AA596783 | mouse |
|  | AA896877 | mouse |
| 1103–1361 | AA356773 | human |
| 1362–1781 | AA573318 | human |
|  | AA179345 | human |
| 1782–1792 | AA186804 | human |
| 1793–1848 | c18854 | human |

In an alternative approach to isolating mammalian ERO1 sequences, the motifs described above may be used to design degenerate oligonucleotide probes to probe large genomic or cDNA libraries directly. General methods for designing and preparing such probes are provided, for example, in Ausubel et al., *Current Protocols in Molecular Biology*, 1996, Wiley & Sons, New York, N.Y.; and *Guide to Molecular Cloning*

*Techniques,* 1987, S. L. Berger and A. R. Kimmel, eds., Academic Press, New York. These oligonucleotides are useful for Ero1 gene isolation, either through their use as probes for hybridizing to Ero1 complementary sequences or as primers for various polymerase chain reaction (PCR) cloning strategies. If a PCR approach is utilized, the primers are optionally designed to allow cloning of the amplified product into a suitable vector, PCR is particularly useful for screening cDNA libraries from rare tissue types.

Hybridization techniques and procedures are well known to those skilled in the art and are described, for example, in Ausubel et al., supra, and *Guide to Molecular Cloning Techniques,* supra. If desired, a combination of different oligonucleotide probes may be used for the screening of the recombinant DNA library. The oligonucleotides are, for example, labelled with $^{32}$P using methods known in the art, and the detectably-labelled oligonucleotides are used to probe filter replicas from a recombinant DNA library. Recombinant DNA libraries (for example, human cDNA libraries) may be prepared according to methods well known in the art, for example, as described in Ausubel et al., supra, or may be obtained from commercial sources. Preferred libraries for isolating mammalian Ero1 homologs include, without limitation, human and murine cDNA libraries from various tissues, and human and murine genomic libraries. Such libraries may be generated using standard techniques, and are also commercially available (from, e.g., Clontech Laboratories, Inc.)

For detection or isolation of closely related ERO1 sequences, high stringency hybridization conditions may be employed; such conditions include hybridization at about 42° C. and about 50% formamide; a first wash at about 65° C., about 2×SSC, and 1% SDS; followed by a second wash at about 65° C. and about 0.1% SDS, 1×SSC. Lower stringency conditions for detecting ERO1 genes having less sequence identity to the yeast ERO1 genes described herein include, for example, hybridization at about 42° C. in the absence of formamide; a first wash at about 42° C., about 6×SSC, and about 1% SDS; and a second wash at about 50° C., about 6×SSC, and about 1% SDS.

As discussed above, ERO1-specific oligonucleotides may also be used as primers in PCR cloning strategies. Such PCR methods are well known in the art and are described, for example, in *PCR Technology,* H. A. Erlich, ed., Stockton Press, London, 1989; *PCR Protocols: A Guide to Methods and Applications,* M. A. Innis, D. H. Gelfand, J. J. Sninsky, and T. J. White, eds., Academic Press, Inc., New York, 1990; and Ausubel et al., supra. Again, sequences corresponding to conserved regions in an Ero1 sequence (for example, those regions described above) are preferred for use in isolating mammalian Ero1 sequences. Such probes may be used to screen cDNA as well as genomic DNA libraries.

Following isolation of such candidate genes by sequence homology, the genes may be tested for their ability to functionally complement a yeast Ero1 mutation (e.g., ero1-1). This is most readily assayed by transformation of the sequence into an Ero1 conditional mutant strain and testing for viability under restrictive conditions. Exemplary yeast transformation techniques are described, for example, in Kaiser et al., *Methods in Yeast Genetics,* 1994, Cold Spring Harbor Laboratory Press, Cold Spring Harbor, N.Y., and assays for Ero1 function are described herein. In evaluating sequences by this approach, a mammalian sequence need not fully complement a yeast Ero1 defect, but must preferably provide a detectable level of functional complementation. Alternatively, a sequence may be tested for function in any standard protein reduction assay, for example, the insulin reduction assay described in Holmgren et al., J. Biol. Chem. 254: 9627–9632, 1979.

Ero1 Polypeptide Expression

In general, Ero1 polypeptides according to the invention may be produced by transformation of a suitable host cell with all or part of an Ero1-encoding cDNA fragment (e.g., one of the cDNAs described herein or isolated as described above) in a suitable expression vehicle.

Those skilled in the field of molecular biology will understand that any of a wide variety of expression systems may be used to provide the recombinant protein. The precise host cell used is not critical to the invention. The Ero1 polypeptide may be produced in a prokaryotic host (e.g., *E. coli*) or in a eukaryotic host (e.g., *Saccharomyces cerevisiae,* insect cells, e.g., Sf9 or Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., 1985, Supp. 1987).

Alternatively, an Ero1 polypeptide is produced in a mammalian system, for example, by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the Ero1 protein is cloned into an expression vector which includes the dihydrofolate reductase (DHFR) gene. Integration of the plasmid and, therefore, the Ero1 protein-encoding gene into the host cell chromosome is selected for by inclusion of 0.01–300 μM methotrexate in the cell culture medium (as described in Ausubel et al., supra). This dominant selection may be accomplished in most cell types. Recombinant protein expression may be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

In yet other alternative approaches, the Ero1 polypeptide is produced in vivo or, preferably, in vitro using a T7 system (see, for example, Ausubel et al., supra, or other standard techniques).

Once the recombinant Ero1 protein is expressed, it is isolated, e.g., using affinity chromatography. In one example, an anti-Ero1 protein antibody (e.g., produced as described herein) may be attached to a column and used to isolate the Ero1 protein. Lysis and fractionation of Ero1 protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Bio-* chemistry And Molecular Biology, eds., Work and Burdon, Elsevier, 1980).

Polypeptides of the invention, particularly short Ero1 polypeptide fragments, may also be produced by chemical synthesis (e.g., by the methods described in Solid Phase Peptide Synthesis, 2nd ed., 1984, The Pierce Chemical Co., Rockford, Ill.).

These general techniques of polypeptide expression and purification may also be used to produce and isolate useful Ero1 fragments or analogs (described herein).

Anti-Ero1 Antibodies

Using the Ero1 polypeptide described herein or isolated as described above, anti-Ero1 antibodies may be produced by any standard technique. In one particular example, an Ero1 cDNA or cDNA fragment encoding a conserved Ero1 domain is fused to GST, and the fusion protein produced in E. coli by standard techniques. The fusion protein is then purified on a glutathione column, also by standard techniques, and is used to immunize rabbits. The antisera obtained is then itself purified on a GST-Ero1 affinity column and is shown to specifically identify GST-Ero1, for example, by Western blotting.

Polypeptides for antibody production may be produced by recombinant or peptide synthetic techniques (see, e.g., Solid Phase Peptide Synthesis, supra; Ausubel et al., supra).

For polyclonal antisera, the peptides may, if desired, be coupled to a carrier protein, such as KLH as described in Ausubel et al, supra. The KLH-peptide is mixed with Freund's adjuvant and injected into guinea pigs, rats, or preferably rabbits. Antibodies may be purified by any method of peptide antigen affinity chromatography.

Alternatively, monoclonal antibodies may be prepared using an Ero1 polypeptide (or immunogenic fragment or analog) and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In: Monoclonal Antibodies and T Cell Hybridomas, Elsevier, N.Y., 1981; Ausubel et al., supra).

Once produced, polyclonal or monoclonal antibodies are tested for specific Ero1 recognition by Western blot or immunoprecipitation analysis (by the methods described in Ausubel et al., supra). Antibodies which specifically recognize an Ero1 polypeptide described herein are considered to be useful in the invention.

Using such techniques, an antibody specific for the yeast Ero1 polypeptide has been isolated.

Use of Ero1 in Eukaryotic Expression Systems

Because of their ability to catalyze disulfide bond formation, Ero1 proteins may be used to improve the yield of properly folded, disulfide bond-containing proteins of interest, for example, commercially important recombinant proteins. Ero1 techniques may be carried out either in vivo or in vitro and exemplary Ero1-based methods of protein production are now described.

In Vitro Refolding Reactions

In general, this approach involves the use of purified Ero1 in combination with any in vitro refolding reaction. In one particular example, a recombinant protein of interest is expressed (for example, in an E. coli or mammalian cell culture system) and is treated with a denaturant, such as guanidine hydrochloride. The protein preparation is then allowed to refold by dilution of the denaturant, and proper disulfide bond formation is promoted during this renaturation step by the presence of Ero1 protein in the reaction mixture. If desired, the Ero1 protein may be added in a buffer combined with oxidized and reduced glutathione and/or purified PDI.

In Vivo Expression Systems

Ero1 may also be used to catalyze proper disulfide bond formation in any in vivo protein expression system. By this approach, a full-length Ero1-expressing cDNA is introduced into a host cell which also expresses a secreted protein of interest. Preferably, the cDNA encodes the Ero1 protein which corresponds most closely to the protein of interest (for example, human Ero1 is preferably expressed in a cell culture for production of a human protein of interest), and the Ero1 is preferably produced at high levels in the cultured cells. Although mammalian tissue culture cells are preferred for this purpose, any appropriate eukaryotic cell may be used for protein expression in conjunction with an Ero1 product. This technique may be used for the production of any protein which is naturally secreted by a eukaryotic cell or which may be joined to a heterologous signal sequence that artificially directs secretion of the protein from the host cell.

Screens for Compounds that Alter the Oxidizing Potential of the Endoplasmic Reticulum The Ero1 reagents provided herein facilitate the development of a variety of screens to identify compounds that can alter the oxidizing potential of the endoplasmic reticulum (ER). Compounds that can either increase or decrease the oxidizing potential of the ER allow for the fine-tuning of an in vivo or in vitro expression system for a particular protein. For example, by carefully modifying the oxidizing potential of the ER in vivo, a cell may be manipulated to selectively over-express a correctly folded recombinant protein, while having a reduced level of expression of an incorrectly folded endogenous protein or a reduced level of formation of insoluble protein aggregates. Likewise, such an oxidizing potential-modifying compound may be added to in vitro expression systems to maximize the correct folding of a denatured protein substrate of interest.

In one particular example of a preferred screen, a yeast cell bearing a temperature sensitive Ero1 mutation, such as the ero1-1 mutant described above, may be utilized to identify a compound that reduces the oxidizing potential of the ER. In this example, a wild-type yeast and an ero1-1 mutant yeast are each exposed to a candidate compound and then grown at a temperature which is permissive to both the wild-type and mutant cells. Compounds that result in the death of ero1-1 mutant yeast cells, but not in the death of wild-type yeast cells, are selected based on their ability to render the ero1-1 mutant hypersensitive. Such compounds act as inhibitors of Ero1 activity and may be employed to reduce the oxidizing potential of the ER, for example, in in vivo or in vitro expression systems.

Other Embodiments

In other embodiments, the invention includes any protein which possesses the requisite level of amino acid sequence identity (as defined herein) to the yeast Ero1 sequence; such homologs include other substantially pure naturally-occurring mammalian Ero1 polypeptides (for example, human Ero1 polypeptides) as well as allelic variants; natural mutants; induced mutants; proteins encoded by DNA that hybridizes to the ERO1 DNA sequence or degenerate conserved domains of Ero1 proteins (e.g., those described herein) under high stringency conditions; and proteins specifically bound by antisera directed to an Ero1 polypeptide.

The invention further includes analogs of any naturally-occurring Ero1 polypeptides. Analogs can differ from the naturally-occurring protein by amino acid sequence differences which do not destroy function, by post-translational modifications, or by both. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring Ero1 polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes Ero1 polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of such Ero1 polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events). For certain purposes, all or a portion of an Ero1 polypeptide sequence may be fused to another protein (for example, by recombinant means).

All publications and patent applications mentioned in this specification are herein incorporated by reference to the same extent as if each independent publication or patent application was specifically and individually indicated to be incorporated by reference.

Other embodiments are within the following claims.

What is claimed is:

1. A method of increasing disulfide bond formation in a protein, said method comprising:
   (a) denaturing said protein; and
   (b) allowing renaturation of said protein in the presence of a eukaryotic Ero1 polypeptide that is encoded by a nucleic acid molecule that specifically hybridizes under high stringency conditions to the complement of the sequence encoding SEQ ID NO: 9, wherein said eukaryotic Ero1 polypeptide promotes disulfide bond formation;
   thereby increasing disulfide bond formation in said protein.

2. The method of claim 1, wherein said Ero1 polypeptide is combined with a protein disulfide-isomerase.

3. A method of increasing disulfide bond formation in a protein, said method comprising expressing said protein in a host cell that also expresses an isolated nucleic acid molecule that specifically hybridizes under high stringency conditions to the complement of the sequence encoding SEQ ID NO: 9, wherein said nucleic acid molecule encodes a eukaryotic Ero1 polypeptide that promotes disulfide bond formation, thereby increasing disulfide bond formation in said protein.

4. The method of claim 3, wherein said host cell further expresses a nucleic acid encoding a protein disulfide-isomerase.

5. The method of claim 1 or 3, wherein said protein is a secreted protein.

6. The method of claim 1 or 3, wherein said eukaryotic Ero1 polypeptide is derived from a yeast.

7. A method of increasing disulfide bond formation in a protein, said method comprising:
   (a) denaturing said protein; and
   (b) allowing renaturation of said protein in the presence of a eukaryotic Ero1 polypeptide comprising an amino acid sequence that is selected from the group consisting of SEQ ID NOs: 2 and 29, wherein said eukaryotic Ero1 polypeptide promotes disulfide bond formation;

thereby increasing disulfide bond formation in said protein.

8. A method of increasing disulfide bond formation in a protein, said method comprising:
   (a) denaturing said protein; and
   (b) allowing renaturation of said protein in the presence of a eukaryotic Ero1 polypeptide that is encoded by a nucleic acid molecule comprising a sequence that is selected from the group consisting of SEQ ID NOs: 1 and 28, wherein said eukaryotic Ero1 polypeptide promotes disulfide bond formation;

thereby increasing disulfide bond formation in said protein.

9. A method of increasing disulfide bond formation in a protein, said method comprising expressing said protein in a host cell that also expresses an isolated nucleic acid molecule that encodes a eukaryotic Ero1 polypeptide comprising an amino acid sequence that is selected from the group consisting of SEQ ID NOs: 2 and 29, wherein said eukaryotic Ero1 polypeptide promotes disulfide bond formation, thereby increasing disulfide bond formation in said protein.

10. A method of increasing disulfide bond formation in a protein, said method comprising expressing said protein in a host cell that also expresses an isolated nucleic acid molecule comprising a nucleotide sequence that is selected from the group consisting of SEQ ID NOs: 1 and 28, wherein said nucleic acid molecule encodes a eukaryotic Ero1 polypeptide that promotes disulfide bond formation, thereby increasing disulfide bond formation in said protein.

* * * * *